United States Patent [19]

App et al.

[11] Patent Number: 5,792,771
[45] Date of Patent: Aug. 11, 1998

[54] QUINAZOLINE COMPOUNDS AND COMPOSITIONS THEREOF FOR THE TREATMENT OF DISEASE

[75] Inventors: Harald App, Hillsborough; Gerald M. McMahon, San Francisco; Peng Cho Tang, Moraga, all of Calif.; Aviv Gazit, Jerusalem, Israel; Alexander Levitzki, Patomic, Mass.

[73] Assignees: Sugen, Inc., Redwood City, Calif.; Yissum Research Development Co. of the Hebrew University of Jerusalem, Jerusalem, Israel

[21] Appl. No.: 462,391

[22] Filed: Jun. 5, 1995

Related U.S. Application Data

[63] Continuation-in-part of Ser. No. 386,021, Feb. 9, 1995, Pat. No. 5,712,395, which is a continuation-in-part of Ser. No. 193,829, Feb. 9, 1994, which is a continuation-in-part of Ser. No. 38,596, Mar. 26, 1993, abandoned, which is a continuation-in-part of Ser. No. 975,750, Nov. 13, 1992, abandoned.

[51] Int. Cl.$^6$ ............... A61K 31/505; A61K 31/495; C07D 239/93; C07D 239/94
[52] U.S. Cl. ............... 514/259; 544/287; 544/293; 544/354; 544/356; 544/250
[58] Field of Search ............... 514/259; 544/291–293, 544/287

[56] References Cited

U.S. PATENT DOCUMENTS

| | | | |
|---|---|---|---|
| 4,966,849 | 10/1990 | Vallee et al. | 514/454 |
| 5,217,999 | 6/1993 | Levitzki et al. | 514/613 |
| 5,281,619 | 1/1994 | Dell et al. | 435/199 |
| 5,302,606 | 4/1994 | Spada et al. | 514/357 |
| 5,330,992 | 7/1994 | Eissenstat et al. | 514/312 |
| 5,457,105 | 10/1995 | Barker | 514/234.5 |

FOREIGN PATENT DOCUMENTS

| | | |
|---|---|---|
| 1 135 471 | 8/1962 | Denmark . |
| 520 722 | 12/1992 | European Pat. Off. . |
| 566 226 | 10/1993 | European Pat. Off. . |
| 55-167205 | 12/1980 | Japan . |
| 60-97964 | 5/1985 | Japan . |
| WO 91/15495 | 10/1991 | WIPO . |
| WO 92/03459 | 3/1992 | WIPO . |
| WO 92/14748 | 9/1992 | WIPO . |
| WO 92/17486 | 10/1992 | WIPO . |
| WO 92/20642 | 11/1992 | WIPO . |
| WO 92/21660 | 12/1992 | WIPO . |
| WO 94/03427 | 2/1994 | WIPO . |
| WO 94/10202 | 5/1994 | WIPO . |
| WO 94/14808 | 7/1994 | WIPO . |

OTHER PUBLICATIONS

Anafi, Mordechai et al., "Selective Interactions of Transforming and Normal abl Proteins with ATP, Tyrosine-Copolymer Substrates, and Tyrphostins", *The Journal of Biological Chemistry*, 7:4518–4523 (1992).

Arvidsson, Ann-Kristin et al., "Tyr-716 in the Platelet-Derived Growth Factor β-Receptor Kinase Insert is Involved in GRB2 Binding Ras Activation", *Mol. & Cell. Bio.*, 14:6715–6726 (1994).

Bolen, Joseph B., "Nonreceptor Tyrosine Protein Kinases", *Oncogene*, 8:2025–2031 (1993).

Breier, Georg et al., "Expression of Vascular Endothelial Growth Factor During Embryonic Angiogenesis and Endothelial Cell Differentiation", *Development*, 114:531 (1992).

De Vries, Carlie et al., "The fms-Like Tyrosine Kinase, a Receptor for Vascular Endothelial Growth Factor", *Science*, 255:989–991 (1992).

Fantl, Wendy et al., "Distinct Phosphotyrosines on a Growth Factor Receptor Bind to Specific Molecules that Mediate Different Signaling Pathways", *Cell*, 69:413–423 (1992).

Folkman and Shing, "Angiogenesis", *The Journal of Biological Chemistry*, 267(16):10931–10934 (1992).

Folkman, M. Judah, "Antiangiogenesis", *Alternative Strategies for Biologic Therapy*, 743–753, (1971).

Folkman, Judah, "Tumor Angiogenisis: Theraputic Implications", *New England Journal of Medicine*, 285:1182–1186 (1971).

Folkman, Judah, "What Is the Evidence That Tumors Are Angiogenesis Dependent?", *J. National Cancer Inst.*, 82:4–6 (1990).

Gazit, Aviv et al., "Tyrphostins. 2. Heterocyclic and α-Substituted Benzylidenemalononitrile Tyrphostins as Potent Inhibitors of EGF Receptor and ErB2/neu Tyrosine Kinases", *Journ. Med. Chem.* , 34:1896–1907 (1991).

Houck, Keith A. et al., "Dual Regulation of Vascular Endothelial Growth Factor Bioavailability by Genetic and Proteolytic Mechanisms", *The Journal of Biological Chemistry*, 267:26031–26037 (1992).

(List continued on next page.)

*Primary Examiner*—Matthew V. Grumbling
*Attorney, Agent, or Firm*—Pennie & Edmonds LLP

[57] ABSTRACT

The present invention relates to organic molecules capable of modulating tyrosine kinase signal transduction and particularly KDR/FLK-1 receptor signal transduction in order to regulate and/or modulate vasculogenesis and angiogenesis. The invention is based, in part, on the demonstration that KDR/FLK-1 tyrosine kinase receptor expression is associated with endothelial cells and the identification of vascular endothelial growth factor (VEGF) as the high affinity ligand of FLK-1. These results indicate a major role for KDR/FLK-1 in the signaling system during vasculogenesis and angiogenesis. Engineering of host cells that express FLK-1 and the uses of expressed FLK-1 to evaluate and screen for drugs and analogs of VEGF involved in FLK-1 modulation by either agonist or antagonist activities is also described.

The invention also relates to the use of the disclosed compounds in the treatment of disorders, including cancer, diabetes, hemangioma and Kaposi's sarcoma, which are related to vasculogenesis and angiogenesis.

12 Claims, No Drawings

OTHER PUBLICATIONS

Hu, P. et al., "Interaction of Phosphatidylinositiol 3-Kinase-Associated p85 with Epidermal Growth Factor and Platelet-Derived Growth Factor Receptors", *Mol. and Cellular Bio.*, 12:981-990 (1992).

Jellinek, Derek et al., "Inhibition of Receptor Binding by High Affinity RNA Ligands to Vascular Endothelial Growth Factor", *Biochemistry*, 33:10450-10456 (1994).

Kashishian, Adam et al., "Phosphorylation Sites in the PDGF Receptor with Different Specifications for Binding GAP and P13 Kinase", *EMBO Journal*, 11:1373-1382 (1992).

Kashishian and Cooper, "Phosphorylation Sites at the C-terminus of the Platelet-Derived Growth Fator Receptor Bind Phospholipase Cγ1 ", *Molecular Bio. of the Cell*, 4:49-57 (1993).

Kaur, Gurmeet et al., "Tyrphostin induced growth inhibition: correlation with effect on $p210^{bcr-abl}$ autokinase activity in K562 chronic myelogenous leukemia", *Anti-Cancer Drugs*, 5:213-222 (1994).

Kazlauskas, Andrius et al., "The 64-kDa protein that Associates with the Platelet-Derived Growth Factor Receptor βSubunit Via Tyr-1009 is the SH2-Containing Phosphotyrosine Phosphatase Syp", *Proc. Natl. Acad. Sci. USA*, 90:6939-6942 (1993).

Kendall, Richard L. et al., "Inhibition of Vascular Endothelial Cell Growth Factor Activity by an Endogenously Encoded Soluble Receptor", *Proc. Natl. Acad. Sci. USA*, 90:10705-10709 (1993).

Kim, K. Jin et al., "Inhibition of Vascular Endothelial Growth Factor-Induced Angiogenesis Blocks Tumor Growth in vivo", *Nature*, 362:841-846 (1993).

Kinsella, J. L. et al., "Protein Kinase C Regulates Endothelial Cell Tube Formation on Basement Membrane Matrix, Matrigel", *Exp. Cell Research*, 199:56-62 (1992).

Klagsbrun and Soker, "VEGF/VPF: The Angiogenesis Factor Found?", *Current Biology*, 3(10):699-702 (1993).

Koch, C. Anne et al., "SH2 and SH3 Domains: Elemnts that Control Interactions of Cytoplasmic Signaling Proteins", *Science*, 252:668-252 (1991).

Kondo, Shinichi et al., "Significance of Vascular Endothelial Growth Factor/Vascular Permeability Factor for Solid Tumor Growth, and its Inhibition by the Antibody", *Biochemical and biophysical Research Communications*, 194(3):1234-1241 (1993).

Liotta, Lance A. et al., "Cancer Metastasis and Angiogenesis: An Imbalance of Positive and Negative Regulation", *Cell*, 64:327-336 (1991).

Maglione, Domenico et al., "Isolation of a human placenta cDNA coding for a protein related to the vascular permeability factor", *Proc. Natl. Acad. Sci. USA*, 88:9267-9271 (1991).

Mariani, M. et al., "Inhibition of Angiogenesis by FCE 26806, A Potent Tyronase Kinase Inhibitor", *Proc. of the Am. Assoc. for Cancer Research*, 35:381 abstract #2268 (1994).

Matthews, William et al., "A Receptor Tyrosine Kinase cDNA Isolated from a Population of Enriched Primitive Hematopoietic Cells and Exhibiting Close Genetic Linkage to c-kit", *Proc. Natl. Acad. Sci, USA*, 88:9026-9030 (1991).

Millauer, Birgit et al., "Glioblastoma Growth Inhibited in vivo by a Dominant-Negative Flk-1 Mutant", *Nature*, 367:576-579 (1994).

Nishimura, R. et al., "Two Signaling Moleculeds Share a Phosphotyrosine-Containing Binding Site in the Platelet Derived Growth Factor Receptor", *Molecular and Cellular Biology*, 13:6889-6896 (1993).

Oelrichs, Robert B. et al., "NYK/FLK-1: A Putative Receptor Protein Tyrosine Kinase Isolated from E10 Embryonic Neuroepithelium is Expressed in Endothelial Cells of the Developing Embryo", *Oncogene*, 8:11-18 (1993).

Plate, K.H. et al., "Up-Regulation of Vascular Endothelial Growth Factor and Its Cognate Receptors in a Rat Glioma Model of Tumor Angiogenesis", *Cancer Research*, 53:5822-5827 (1993).

Plowman, Gregory D. et al., "Receptor Tyrosine Kinases as Targets for Drug Intervention", *DN&P*, 7(6):334-339 (1994).

Quinn, Timothy P. et al., "Fetal Liver Kinase 1 is a Receptor for Vascular Endothelial Growth Factor and is Selectively Expressed in Vascular Endothelium", *Proc. Natl. Acad. Sci., USA*, 90:7533-7537 (1993).

Rozakis-Adcock, M. et al., "Association of the Shc and Grb2/Sem5 SH2-Containing Proteins is Implicated in Activation of the Ras Pathway by Tyrosine Kinases", *Nature*, 360:689-692 (1992).

Sarzani, Riccardo et al., "A Novel Endothelial Tyrosinase Kinase cDNA Homologous to Platlet-Derived Growth Factor Receptor cDNA", *Biochemical and Biophysical Research Communications*, 188(2):706-714 (1992).

Schlessinger, J. et al., "Growth Factor Signaling by Receptor Tyrosine Kinases", *Neuron*, 9:383-391 (1992).

Schuchter, Lynn M. et al., "Successful Treatment of Murine Melanoma with Bryostatin 1", *Cancer Research*, 51:682-687 (1991).

Shibuya, Masabumi et al., "Nucleotide Sequence and Expression of a Novel Human Receptor-Type Tyrosine Kinase Gene (flt) closely related to the fms Family", *Oncogene*, 5:519-524 (1990).

Songyang, Zhou et al., "SH2 Domains Recognize Specific Phosphopeptide Sequences", *Cell*, 72:767-778 (1993).

Songyang, Zhou et al., "Specific Motifs Recognized by the SH2 Domains of Csk, 3BP2, fps/fes, GRB-2, HCP, SHC, Syk, and Vav", *Molecular and Cell Bio.*, 14:2777-2785, (1994).

Takano, S. et al., "Inhibition of Angiogenesis by a Novel Diaminoanthraquinone that Inhibits Protein Kinase C", *Mol Bio of the Cell*, 4:358a, abstract #2076, (1993).

Terman, Bruce I. et al., "Indentification of a new endothelial cell growth factor receptor tyrosine kinase". *Oncogene*, 6:1677-1683 (1991).

Terman, Bruce I. et al., "Identification of the KDR Tyrosine Kinase as a Receptor for Vascular Endothelial Cell Growth Factor", *Biochem. Biophys. Res. Commun.*, 187:1579-1586 (1992).

Twamley-Stein, Geraldine M. et al., "The Src Family Tyrosine Kinases are Required for Platelet-Derived Growth Factor-Mediated Signal Transduction in NIH 3T3 Cells", *Proc. Natl. Acad. Sci. USA*, 90:7696-7700 (1993).

Ullrich, et al., "Signal Transduction by Receptors with Tyrosine Kinase Activity" *Cell*, 61:203-212 (1990).

Vaisman, Nora et al., "Characterization of the Receptor for Vascular Endothelial Growth Factor", *J. of Biological Chemistry*, 265:19461-19566 (1990).

Weidner, Noel et al., "Tumor Angiogenesis and Metastasis—Correlation in Invasive Breast Carcinoma", *New England J. of Medicine*, 324:1-7 (1991).

Wright, Paul S. et al., "Inhibition of Angiogenesis In Vitro and In Ovo with and Inhibitor of Cellular Protein Kinases, MDL 27032", *J. of Cellular Physiology*, 152:448–457 (1992).

Yamaguchi, Terry P. et al., "flk–1, an flt–Related Receptor Tyrosine Kinase is an Early Marker for Endothelial Cell Precursors", *Development*, 118:489–498 (1993).

Gazit, Aviv et al., "Tyrphostins. 3. Structure–Activity relationship Studies of α–Substituted Benzylidenemalononitrile 5–S–Aryltyrphostins", *J. Med. Chem.*, 36:3556–3564 (1993).

Kokosi, Jozsef et al., "Process for producing imidazo[5,1-b]quinazolin–9–one derivatives and pharmaceutically acceptable salts thereof, as well as pharmaceutical compositions comprising such as active ingredient", *Chemical Abstracts*, vol. 117, abstract No. 212519, (1990).

Merlin, Jean Claude et al., "Resonance Raman study of phenylhydrazonopropanedinitriles", *Can. J. Chem.*, 63:1840:1844 (1985).

Miyoshi, Hideto et al., "Quantitative analyses of the uncoupling activity of substituted phenols with mitochondria from flight muscles of house flies", *Biochimica et Biophysica Acta*, 935:312–321 (1988).

Ohmichi, Masahide et al., "The Tyrokinase Kinase Inhibitor Tyrphostin Blocks the Cellular Actions of Nerve Growth Factor", *Biochemistry*, 32:4650–4658 (1993).

Stout, David M. et al., "Synthesis and Antiarrhythmic and Parasympatholytic Properties of Substituted Phenols. 1. Heteroarylamine Derivatives", *J. Med. Chem.*, 26:808–813 (1983).

Vogel, M. et al., "Synthese von–4–substituierten 1,2,3–Triazolo[1,5–a]–chinoxalinen[2])", *Journal f. prakt. Chemie*: Band 329, Heft 1:101–107 (1987).

QUINAZOLINE COMPOUNDS AND COMPOSITIONS THEREOF FOR THE TREATMENT OF DISEASE

This application is a continuation-in-part of a U.S. application Ser. No. 08/386,021, filed Feb. 9, 1995, now U.S. Pat. No. 5,712,395, which is a continuation-in-part and divisional of U.S. application Ser. No. 08/193,829, filed Feb. 9, 1994, which is a continuation-in-part of U.S. application Ser. No. 08/038,596, filed Mar. 26, 1993, now abandoned, which is a continuation-in-part of U.S. application Ser. No. 07/975,750, filed Nov. 13, 1992, now abandoned, all three of which are incorporated by reference herein in their entirety.

1. INTRODUCTION

The present invention relates to novel compounds capable of modulating and/or regulating tyrosine kinase signal transduction. The Applicants have demonstrated that the murine fetal liver kinase 1 (FLK-1) receptor and its non-murine counterparts, including the human Kinase Insert-Domain-Containing Receptor (KDR), play a major role in a tyrosine kinase signal transduction system. Polypeptide growth factors such as vascular endothelial growth factor (VEGF) having a high affinity to the KDR/FLK-1 receptor have been associated with the proliferation of endothelial cells and more particularly vasculogenesis and/or angiogenesis. Consequently, compounds affecting the enzymatic function of the KDR/FLK-1 receptor may be used to not only regulate, modulate and/or inhibit the tyrosine kinase signal transduction system, but also the proliferation of endothelial cells in processes such as vasculogenesis and/or angiogeneis. The present invention is therefore further directed to the use of compounds which bind to and/or modulate the activity of the receptors comprising the tyrosine signal transduction system, and more specifically the KDR/FLK-1 receptor, to treat disorders related to vasculogenesis and/or angiogenesis.

2. BACKGROUND OF THE INVENTION

Receptor Tyrosine Kinases.

Receptor tyrosine kinases (RTKS) comprise a large family of transmembrane receptors for polypeptide growth factors with diverse biological activities. The intrinsic function of RTKs is activated upon ligand binding, which results in phosphorylation of the receptor and multiple cellular substrates, and subsequently in a variety of cellular responses. Ullrich & Schlessinger, 1990, *Cell* 61:203–212.

As has been reported by the inventors, RTKs, as well as, more generally, protein tyrosine kinases, play an important role in the control of cell growth and differentiation (for review, see Schlessinger & Ullrich, 1992, *Neuron* 9:383–391). Aberrant expression or mutations in the RTKs have been shown to lead to either uncontrolled cell proliferation (e.g. malignant tumor growth) or to defects in key developmental processes. Consequently, the biomedical community has expended significant resources to discover the specific biological role of members of the RTK family, their function in differentiation processes, their involvement in tumorigenesis and in other diseases, the biochemical mechanisms underlying their signal transduction pathways activated upon ligand stimulation and the development of novel antineoplastic drugs.

At present, at least nineteen (19) distinct RTK subfamilies have been identified. One RTK subfamily is believed to be comprised of the KDR/FLK-1 receptor, the fetal liver kinase 4 (FLK-4) receptor and the fms-like tyrosine 1 (flt-1) receptor. Each of these receptors was initially believed to be receptors for hematopoietic growth factors.

The KDR/FLK-1 Receptor and VEGF.

Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman & Shing, 1992, *J. Biological Chem.* 267(16):10931–34. Uncontrolled vasculogenesis and/or angiogenesis has been associated with diseases, such as diabetes, as well as malignant solid tumors that rely on vascularization for growth. Klagsburn & Soker, 1993, *Current Biology* 3(10):699–702; Folkham, 1991, *J. Natl., Cancer Inst.* 82:4–6; Weidner, et al., 1991, *New Engl. J. Med.* 324:1–5.

Several polypeptides with in vitro endothelial cell growth promoting activity have been identified. Examples include acidic and basic fibroblastic growth factor (FGF), vascular endothelial growth factor (VEGF) and placental growth factor. Unlike FGF, VEGF has recently been reported to be an endothelial cell specific mitogen. Ferrara & Henzel, 1989, *Biochem. Biophys. Res. Comm.* 161:851–858; Vaisman et al., 1990, *J. Biol. Chem.* 265:19461-19566.

Thus, identification of the scpecific receptors to which VEGF binds is important to understanding of the regulation of endothelial cell proliferation. Two structurally related RTKs have been identified to bind VEGF with high affinity: the flt-1 receptor (Shibuya et al., 1990, *Oncogene* 5:519–524; De Vries et al., 1992, *Science* 255:989–991) and the KDR/FLK-1 receptor, discussed herein. Consequently, it had been surmised that RTKs may have a role in the modulation and regulation of endothelial cell proliferation.

As has only been recently contemplated, evidence, such as information set forth in U.S. application Ser. Nos. 08/193, 829, 08/038,596 and 07/975,750, strongly suggest that VEGF is not only responsible for endothelial cell proliferation, but also is the prime regulator of normal and pathological angiogenesis. See generally, Klagsburn & Soker, 1993, *Current Biology* 3(10)699–702; Houck, et al., 1992, *J. Biol. Chem.* 267:26031-26037.

Identification Of Agonists Arid Antagonists To The KDR/FLK-1 Receptor.

In view of the surmised importance of RTKs to the control, regulation and modulation of endothelial cell proliferation and potentially vasculogenesis and/or angiogenesis, many attempts have been made to identify RTK "inhibitors" using a variety of approaches, including the use of mutant ligands (U.S. application Ser. No. 4,966, 849), soluble receptors and antibodies (Application No. WO 94/10202; Kendall & Thomas, 1994, *Proc. Nat'l Acad. Sci* 90:10705–09; Kim, et al., 1993, *Nature* 362:841–844), RNA ligands (Jellinek, et al., *Biochemistry* 33:10450–56), protein kinase C inhibitors (Schuchter, et al., 1991, *Cancer Res.* 51:682–687); Takano, et al., 1993, *Mol. Bio. Cell* 4:358A; Kinsella, et al., 1992, *Exp. Cell Res.* 199:56–62; Wright, et al., 1992, *J. Cellular Phys.* 152:448–57) and tyrosine kinase inhibitors (WO 94/03427; WO 92/21660; WO 91/15495; WO 94/14808; U.S. Pat. No. 5,330,992; Mariani, et al., 1994, *Proc. Am. Assoc. Cancer Res.* 35:2268).

More recently, attempts have been made to identify small molecules which act: as tyrosine kinase inhibitors. For example, bis monocyclic, bicyclic or heterocyclic aryl compounds (PCT WO 92/20642), vinylene-azaindole derivatives (PCT WO 94/14808) and 1-cycloproppyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer. None of these compounds, however, have been previously associated with the enzymatic function of the KDR/FLK-1 receptor. Likewise, none of these compounds have been associated with regulation of vasculogenesis and/or angiogenesis.

The identification of effective small compounds which specifically inhibit tyrosine signal transduction by modulating the activity of RTKs and particularly the KDR/FLK-1 receptor to regulate and modulate vasculogenesis and/or angiogenesis is therefore desirable and the object of this invention.

3. SUMMARY OF THE INVENTION

The present invention relates to organic molecules capable of modulating tyrosine signal transduction and the use of such molecules to inhibit or promote angiogenesis and/or vasculogenesis. Generally, the compounds of the instant invention are derivatives of quinazoline, quinoxaline, substituted aniline, isoxazoles, acrylonitrile and phenylacrylonitrile compounds. More specifically, the invention is generally directed to compounds having the formulae:

A.

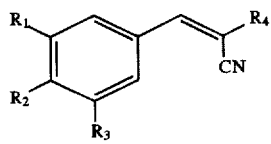

and pharmaceutically acceptable salts thereof, wherein:
$R_1$ is isopropyl, t-butyl, I, Br, OH or methyl,
$R_2$ is OH,
$R_3$ is 2-propyl, t-butyl, OH, H or methyl, and
$R_4$ is (1-phenyl)-n-propylaminocarbonyl, (E) 1-cyano-2-[(3,5-diisopropyl-4-hydroxy)phenyl]ethenylsulfonyl, aminothiocarbonyl, cyanomethylsufonyl, (3-amino-4-cyano)pyrazo-5-yl, phenyl-n-propylaminocarbonyl, (E) 1-cyano-2-[(5-bromo-3,4-dihydroxy)phenyl]ethenylsulfonyl, (1-phenyl)-n-propylaminothiocarbonyl, cyano, (E) [[[4-[1-cyano-2 (3,4-dihydroxy)phenyl]ethenyl]carbonylamino]-n-butyl]aminocarbonyl, benzylaminocarbonyl, 2[[2-cyano-1-(3,4-dihydroxy)phenyl]ethylenyl]]sulfonyl, [(3,4-dihydroxy)phenyl]carbonyl, (E) [[[4-[1-cyano-2 (3,4-dihydroxy)phenyl]ethenyl]carbonylamino]-ethyl] aminocarbonyl or hydroxycarbonyl;

—OR—

B.

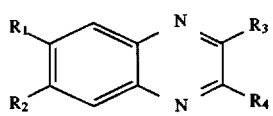

and pharmaceutically acceptable salts thereof, wherein:
$R_1$ is $CH_3$ or H, $R_2$ is $CH_3$ or H, or alternatively,
$R_1$ and $R_2$ form a phenyl ring (CHCHCHCH),
$R_3$ is H or formyl or chloro, and
$R_4$ is phenyl, (3,4-dihydroxy)phenyl, (4-iodophenyl) amino, (3,4-dichlorophenyl)amino, (3-chlorophenyl) amino, (4-bromophenyl)amino or n-propylamino;

—OR—

C.

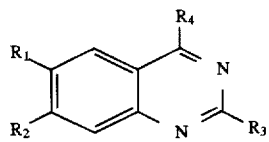

and pharmaceutically acceptable salts thereof, wherein:
$R_1$ is $OCH_3$, $CH_3$ or H,
$R_2$ is $OCH_3$ or H,
$R_3$ is H or chloro, and
$R_4$ is (3-chlorophenyl)amino, (4-methylphenyl)mecapto, (4-iodophenyl)amino or (3-hydroxyphenyl)amino;

—OR—

D.

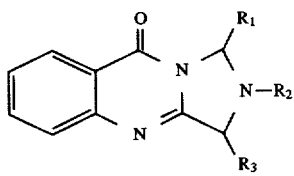

and pharmaceutically acceptable salts thereof, wherein:
$R_1$ is 4-hydroxy-phenyl
$R_2$ is benzyl, and
$R_3$ is $CH_3$;

—OR—

E.

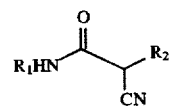

and pharmaceutically acceptable salts thereof, wherein:
$R_1$ is (3-trifluormethyl)phenyl and
$R_2$ is (2-chlorophenyl)aminothiocarbonyl;

—OR—

F.

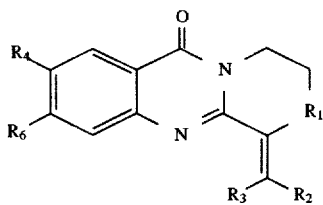

and pharmaceutically acceptable salts thereof, wherein:

$R_1$ is O, $R_2$ is (3,4-dihydroxyphenyl), and $R_3$, $R_4$ and $R_5$ are H;

—OR—

G.

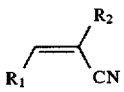

and pharmaceutically acceptable salts thereof, wherein:

$R_1$ is 4-(1-nitro)thiophene or indol-3-yl or indol-5-yl and $R_2$ is aminothiocarbonyl, (3-amino-4-cyano)pyrazol-5-yl or (3,4-dihydroxyphenyl)carbonyl;

—OR—

H.

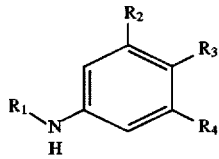

and pharmaceutically acceptable salts thereof, wherein:

$R_1$ is 2,5-dihydroxylbenzyl, $R_2$ is H, $R_3$ is methoxycarbonyl, and $R_4$ is H;

—OR—

I.

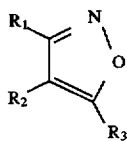

and pharmaceutically acceptable salts thereof, wherein:

$R_1$ is H, $R_2$ is (4-trifluoromethyl)phenyl, and $R_3$ is methyl;

—OR—

J.

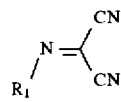

and pharmaceutically acceptable salts thereof, wherein $R_1$ is (3-chloro)phenylamino.

The present invention is further directed to pharmaceutical compositions comprising a pharmaceutically effective amount of the above-described compounds and a pharmaceutically acceptable carrier or excipient. Such a composition is believed to affect the enzymatic activity of the KDR/FLK-1 receptor by, inter alia, inhibiting the signal transduced by interaction between KDR/FLK-1 and vascular endothelial growth factor (VEGF) which may be useful in inhibition of diseases related to vasculogenesis and/or angiogenesis;, including diabetes and cancer. Alternatively, such composition may act directly on the cells responsible for the disease (e.g. tumor cells). More particularly, the compositions of the present invention may be included in methods for treating, among other diseases, diabetic retinopathy, glioma, melanoma, Kaposi's sarcoma, hemangioma and ovarian, breast, lung, pancreatic, prostate, colon and epidermoid cancer. Such a composition, if used to modulate, rather than inhibit, vasculogenesis and/or angiogenesis may also be useful in the promotion of wound healing.

Finally, the present invention is also directed to methods for treating diseases related to pathological vasculogenesis and/or angiogenesis, including but not limited to diabetes, diabetic retinopathy, rheumatoid arthritis, hemangioma and cancer and more particularly cancer related to solid cell tumor growth (e.g., glioblastoma, melanoma and Kaposi's sarcoma and ovarian, lung, mammary, prostate, pancreatic, colon and epidermoid carcinoma).

3.1. Definitions

"Pharmaceutically acceptable acid addition salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Alkyl" refers to a saturated or unsaturated branched or straight chain hydrocarbon radical. Typical alkyl groups includes methyl, ethyl, propyl, isopropyl, butyl, isobutyl, tertiary butyl, pentyl, hexyl and the like.

4. DETAILED DESCRIPTION OF THE INVENTION

The present invention relates to compounds capable of regulating and/or modulating tyrosine signal transduction and more particularly KDR/FLK-1 receptor signal transduction in order to inhibit or promote angiogenesis and/or vasculogenesis.

The present invention is based, in part, on the discovery that the KDR/FLK-1 tyrosine kinase receptor, and RTKs more generally, is expressed on the surface of endothelial cells and may play a role in endothelial cell growth, including solid cell tumor growth. The invention is also based on the identification of VEGF as a high affinity ligand of KDR/FLK-1 and the characterization of KDR/FLK-1 as an RTK rather than a hematopoietic receptor. Thus, the surmised role of VEGF in endothelial cell proliferation and migration during angiogenesis and vasculogenesis indicate an important role for the KDR/FLK-1 in these processes.

The invention is further based on the observation that diseases such as diabetes mellitus (Folkman, 1987, in XIth Congress of Thromboscis and Haemostasis (Verstraeta, et al., eds.) pp. 583–596, Leuven University Press, Leuven) and arthritis, as well as malignant tumor growth may result from uncontrolled angiogenesis. See e.g., Folkman, 1971, N. Engl. J. Med. 285:1182–1186. Finally, the invention is based upon the discovery and design of compounds that inhibit, prevent, or interfere with the signal transduced by KDR/FLK-1 when activated by ligands such as VEGF. Although it is therefore believed that the compounds of the present invention act on a receptor or other component along the tyrosine kinase signal transduction pathway, the compounds may also act directly on the tumor cells that result from uncontrolled angiogenesis.

For purposes of this application, although the nomenclature of the human and murine counterparts of the generic "flk-1" receptor differ, they are, in many respects, interchangeable. The murine receptor, FLK-1, and its human counterpart, KDR, share a sequence homology of 93.4%, within the intracellular domain. Likewise, murine FLK-1 binds human VEGF with the same affinity as mouse VEGF, and accordingly, is activated by the ligand derived from either species. Millauer et al., 1993, Cell 72:835–846; Quinn et al., 1993, Proc. Natl. Acad. Sci. USA 90:7533–7537. FLK-1 also associates with and subsequently tyrosine phosphorylates human RTK substrates (e.g., PLC-γ or p85) when coexpressed in 293 cells (human embryonal kidney fibroblasts).

Models which rely upon the FLK-1 receptor therefore are directly applicable to understanding the KDR receptor. For example, use of the murine FLK-1 receptor in methods to identify compounds which regulate the signal transduction pathway are directly applicable to the identification of compounds which may be used to regulate the human signal transduction pathway, and more specifically, activity related to the KDR receptor. Angiogenesis is a very complex process involving the invasion of endothelial cells into the nonvascularized tissue. No in vitro model exists which mimics exactly this multistep process comprising the degradation of the basal membrane surrounding the endothelial cells, migration into the perivascular stroma and eventually proliferation and formation of the new vascular sprout. Thus, chemical is compounds identified as inhibitors of KDR/FLK-1 in vitro, will be confirmed in suitable in vivo models. Both in vivo mouse and rat animal models have been demonstrated to be of excellent value for the examination of the clinical potential of agents acting on the KDR/FLK-1 induced signal transduction pathway.

In sum, the receptors to which VEGF specifically binds are an important and powerful therapeutical target for the regulation and modulation of vasculogenesis and/or angiogenesis and a variety of severe diseases which involve abnormal cellular growth caused by such processes. Plowman, et al., 1994, DN&P 7(6):334–339. More particularly, the KDR/FLK-1 receptor's high specificity and role in the neovascularization make it a very distinct and powerful target for therapeutic approaches for the treatment of cancer and other diseases which involve the uncontrolled formation of blood vessels.

This invention is therefore directed to compounds which regulate, modulate and/or inhibit vasculogenesis and/or angiogenesis by affecting the enzymatic activity of the KDR/FLK-1 receptor and interfering with the signal transduced by KDR/FLK-1. More particularly, the present invention is directed to compounds which regulate, modulate and/or inhibit the KDR/FLK-1 mediated signal transduction pathway as a therapeutic approach to cure many kinds of solid tumors, including but not limited to glioblastoma, melanoma and Kaposi's sarcoma, and ovarian, lung, mammary, prostate, pancreatic, colon and epidermoid carcinoma. In addition, data suggest the administration of compounds which inhibit the KDR/FLK-1 mediated signal transduction pathway to the treatment of hemangioma and diabetic retinopathy.

The invention also relates to the inhibition of vasculogenesis and angiogenesis via other receptor-mediated pathways, including the pathway comprising the highly related flt-1 receptor. Receptor tyrosine kinase mediated signal transduction is initiated by extracellular interaction with a specific growth factor (ligand), followed by receptor dimerization, transient stimulation of the intrinsic protein tyrosine kinase activity and autophosphorylation. Binding sites are thereby created for intracellular signal transduction molecules and lead to the formation of complexes with a spectrum of cytoplasmic signalling molecules that facilitate the appropriate cellular response, e.g., cell division, metabolic effects to the microenvironment. See, Schlessinger and Ullrich, 1992, Neuron 9:1–20.

It has been shown that tyrosine autophosphorylation sites in growth factor receptors, such as KDR/FLK-1 and flt-1, function as high-affinity binding sites for SH2 (src homology) domains of signaling molecules. Fantl et al., 1992, Cell 69:413–423; Songyang et al., 1994, Mol. Cell. Biol. 14:2777–2785); Songyang et al., 1993, Cell 72:767–778; and Koch et al., 1991, Science 252:668–678. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. Songyang et al., 1993, Cell 72:767–778. The specificity of the interactions between receptors, such as KDR/FLK-1 and flt-1, and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylatiori profiles. Songyang et al., 1993, Cell 72:767–778. These observations suggest that the function of each receptor tyrosine kinase is determined not only by its pattern of expression and ligand availability but also by the array of downstream signal transduction pathways that are activated by a particular receptor. Thus, autophosphorylation provides an important regulatory step which determines the selectivity of signaling pathways recruited by specific growth factor receptors, as well as differentiation factor receptors.

The close homology of the intracellular regions of KDR/FLK-1 with that of the PDGF-β-Receptor (50.3% homolgy) and/or the highly related flt-1 receptor indicates the induction of overlapping signal transduction pathways. For example, for the PDGF-β-Receptor, members of the src family (Twamley et al., 1993, Proc. Natl. Acad. Sci. USA 90:7696–7700), phosphatidylinositol-3'-kinase (Hu et al., 1992, Mol. Cell. Biol. 12:981–990), phospholipase C-γ (Kashishian & Cooper, 1993, Mol. Cell. Biol. 4:49–51), ras-GTPase-activating protein, (Kashishian et al., 1992, EMBO J. 11:1373–1382), PTP-1D/syp (Kazlauskas et al., 1993, Proc. Natl. Acad. Sci. USA 90:6939–6943), Grb2 (Arvidsson et al., 1994, Mol. Cell. Biol. 14:6715–6726), and the adapter molecules Shc and Nck (Nishimura et al., 1993, Mol. Cell. Biol. 13:6889–6896), have been shown to bind to regions involving different autophosphorylation sites. For a general review, please see Claesson-Welsh, 1994, Prog. Growth Factor Res. 5:37–54. Thus, it is likely that signal transduction pathways activated by KDR/FLK-1 include the ras pathway (Rozakis et al., 1992, Nature 360:689–692), the PI-3'-kinase pathway and the src-mediated and plcγ-mediated pathways. Each of these pathways may play a critical role in the angiogenic and/or vasculogenic effect of KDR/FLK-1 in endothelial cells. Consequently, the present invention is also directed to the use of the organic compounds discussed herein to modulate angiogenesis and vasculogenesis as such processes are controlled by these pathways.

4.1. The Compounds

The invention is generally directed to compounds and/or compositions comprising compounds having the formulae:

A.

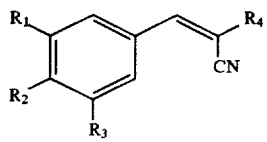

and pharmaceutically acceptable salts thereof, wherein:

$R_1$ is isopropyl, t-butyl, I, Br, OH or methyl,
$R_2$ is OH,
$R_3$ is 2-propyl, t-butyl, OH, H or methyl, and
$R_4$ is (1-phenyl)-n-propylaminocarbonyl, (E) 1-cyano-2-[(3,5-diisopropyl-4-hydroxy)phenyl]ethenylsulfonyl, aminothiocarbonyl, cyanomethylsufonyl, (3-amino-4-cyano)pyrazo-5-yl, phenyl-n-propylaminocarbonyl, (E) 1-cyano-2-[(5-bromo-3,4-dihydroxy)phenyl]ethenylsulfonyl, (1-phenyl)-n-propylaminothiocarbonyl, cyano, (E) [[[4-[1-cyano-2 (3,4-dihydroxy)phenyl] ethenyl]carbonylamino]-n-butyl]aminocarbonyl, benzylaminocarbonyl, 2[[2-cyano-1-(3,4-dihydroxy)phenyl]ethylenyl]]sulfonyl, [(3,4-dihydroxy)phenyl]carbonyl, (E) [[[4-[1-cyano-2 (3,4-dihydroxy)phenyl]ethenyl]carbonylamino]-ethyl] aminocarbonyl or hydroxycarbonyl;

—OR—

B.

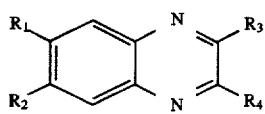

and pharmaceutically acceptable salts thereof, wherein:

$R_1$ is $CH_3$ or H,
$R_2$ is $CH_3$ or H, or alternatively,
$R_1$ and $R_2$ form a phenyl ring (CHCHCHCH),
$R_3$ is H or formyl or chloro, and
$R_4$ is phenyl, (3,4-dihydroxy)phenyl, (4-iodophenyl) amino, (3,4-dichlorophenyl)amino, (3-chlorophenyl) amino, (4-bromophenyl)amino or n-propylamino;

—OR—

C.

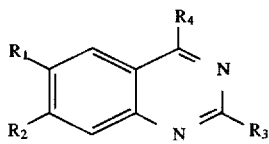

and pharmaceutically acceptable salts thereof, wherein:

$R_1$ is $OCH_3$, $CH_3$ or H,
$R_2$ is $OCH_3$ or H,
$R_3$ is H or chloro, and
$R_4$ is (3-chlorophenyl)amino, (4-methylphenyl)mecapto, (4-iodophenyl)amino or (3-hydroxyphenyl)amino;

—OR—

D.

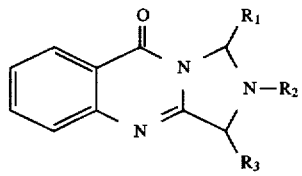

and pharmaceutically acceptable salts thereof, wherein:

$R_1$ is 4-hydroxy-phenyl
$R_2$ is benzyl, and
$R_3$ is $CH_3$:

—OR—

E.

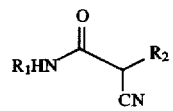

and pharmaceutically acceptable salts thereof, wherein:

$R_1$ is (3-trifluormethyl)phenyl and
$R_2$ is (2-chlorophenyl)aminothiocarbonyl;

—OR—

F.

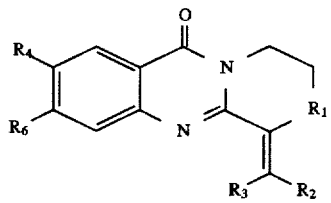

and pharmaceutically acceptable salts thereof, wherein:

$R_1$ is O,
$R_2$ is (3,4-dihydroxy)phenyl, and
$R_3$, $R_4$ and $R_5$ are H;

—OR—

G.

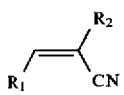

and pharmaceutically acceptable salts thereof, wherein:
$R_1$ is 4-(1-nitro)thiophene or indol-3-yl or indol-5-yl and
$R_2$ is aminothiocarbonyl, (3-amino-4-cyano)pyrazol-5-yl or (3,4-dihydroxyphenyl)carbonyl;

—OR—

H.

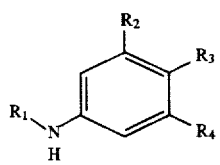

and pharmaceutically acceptable salts thereof, wherein:
$R_1$ is 2,5-dihydroxybenzyl,
$R_2$ is H,
$R_3$ is methoxycarbonyl, and
$R_4$ is H;

—OR—

I.

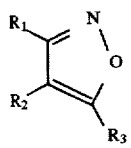

and pharmaceutically acceptable salts thereof, wherein:
$R_1$ is H,
$R_2$ is (4-trifluoromethyl)phenyl, and
$R_3$ is methyl;

—OR—

J.

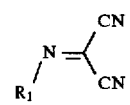

and pharmaceutically acceptable salts thereof, wherein $R_1$ is (3-chloro)phenylamino.

The chemical formulae referred herein may exhibit the phenomenon of tautomerism. As the formulae drawings within this specification can only represent one of the possible tautomeric forms, it should be understood that the invention encompasses any tautomeric form which possesses the ability to regulate and/or modulate vasculogenesis and/or angiogenesis and is not limited to any one tautomeric form utilized within the formulae drawings.

In addition to the above compounds and their pharmaceutically acceptable salts, the invention is further directed, where applicable, to solvated as well as unsolvated forms of the compounds (e.g. hydrated forms) having the ability to regulate and/or modulate vasculogenesis and/or angiogenesis.

The compounds described above may be prepared by any process known to be applicable to the preparation of chemically-related compounds. Suitable processes are illustrated by the following representative examples. Necessary starting materials may be obtained by standard procedures of organic chemistry.

4.2. Pharmaceutical Formulations And Routes Of Administration

The identified compounds can be administered to a human patient, by itself, or in pharmaceutical compositions where it is mixed with suitable carriers or excipient(s) at doses to treat or ameliorate a variety of disorders, including solid cell tumor growth, including Kaposi's sarcoma, glioblastoma, and melanoma and ovarian, lung, mammary, prostate, pancreatic, colon and epidermoid carcinoma, diabetes, diabetic retinopathy, hemangioma and rheumatoid arthritis. A therapeutically effective dose further refers to that amount of the compound sufficient to result in amelioration of symptoms of uncontrolled vasculogenesis and angiogenesis. Techniques for formulation and administration of the compounds of the instant application may be found in "Remington's Pharmaceutical Sciences," Mack Publishing Co., Easton, Pa., latest edition.

4.2.1. Routes Of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Alternately, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

4.2.2. Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration,the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric, or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the KDR/FLK-1 receptor modulating compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

4.2.3. Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the IC50 as determined in cell culture (i.e., the concentration of the test compound which achieves a half-maximal inhibition of the RTK activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds which exhibit high therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1).

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g., the concentration necessary to achieve a 50–90% inhibition of the kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

4.2.4. Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition. Suitable conditions indicated on the label may include treatment of a tumor, such as a glioma or glioblastoma and inhibition of angiogenesis.

5. EXAMPLE: Compound Synthesis 5.1. Synthesis Of (E)-2-aminothiocarbonyl-3-(3,5-di-t-butyl-4-hydroxyphenyl)acrylonitrile A preferred method of synthesis of (E)-2-aminothiocarbonyl-3 (3,5-di-t-butyl-4-hydroxyphenyl) acrylonitrile (Compound 1) is as follows: The compound was prepared as generally described by Ohmichi et al., 1993, Biochemistry 32:4650. A mixture of 0.47 g of 3,5-Di-tert-butyl-4-hydroxybenzaldehyde, 0.2 g of thiocyanoacetamide and 30 mg of β-alanine in 40 ml of ethanol was refluxed for 6 hours. Water and HCl were added, and the reaction mixture was extracted with ethyl acetate. Evaporation gave 0.34 g (54% yield) of a yellow solid having a melting point of 210° C.

The product gave the following analytical data: NMR (acetone-$d_6$) δ 8.47 (1,H, s, vinyl), 8.02 (2H, s), 1.48 (18H, s); MS m/e 316 (M+, 100), 303 (35), 301 (99), 268 (16), 260- (M ($CH_3$)2=C,45) , 245 (17), 228 (22), 219 (52), 203 (10), 143 (11), 129 (11).

5.2. Synthesis Of (E)-2-cyano-3-(3-iodo-4,5-hydroxyphenyl)acrylonitrile

A preferred method of synthesis of (E)-1-cyano-3-(3-iodo-4,5-hydroxyphenyl)acrylonitrile (Compound 2) is as follows: The compound was prepared as described in Ohmichi et al., 1993, Biochemistry 32:4650 in two steps. First, 3-methoxy-4-hydroxy-5-iodobenzylidene malononitrile was prepared by adding 3 drops of piperidine to 1.4 g of 5-iodovanillin and 0.4 g of malononitrile in 25 ml of ethanol and refluxing the mixture for 4 hours. 0.8 g (49% yield) of a yellow solid resulted.

The 3-methoxy-4-hydroxy-5-(iodobenzylidene) malononitrile product gave the following analytical data: mp 188° C.; NMR ($CDCl_3$) δ 7.76 (1HJ=1.8 Hz, H6), 7.65 (1H,dJ=1.8 Hz, H2), 7.56 (1H,s,vinyl), 6.85 (1, H,s, OH), 3.99 (3, H,S, $OCH_3$) ; MS m/e 327 (13) , 326 (M+, 100) , 283 (18) , 128 (35), 101 (22).

Next, (3-methoxy-4-hydroxy-5-iodobenzylidene) malononitrile (0.65 g) and 0.6 ml of boron tribromide ($BBr_3$) in 40 ml of dichloromethane were stirred under argon for 1 hour at room temperature. Water was added, and the reaction mixture was extracted with ethyl acetate to give 0.46 g (73% yield) of a light-red solid (yellow in solution) having a melting point of 105° C.

The final product gave the following analytical data: NMR (acetone-$d_6$) δ 8.03 (1H,s,vinyl), 7.88 (1H,dJ=2.3 Hz, H2), 7.72 (1H,d,J=2.3 Hz, H6); MS m/e 312 (M+, 38), 254 (74), 185 (M—I,27), 158 (M—I-HCN,11), 157 (64), 130 (19), 129 (23), 127 (100).

5.3. Synthesis Of (E)-2-(3-phenyl-n-propylaminocarbonyl)-3-(3-bromo-4,5-diydroxyphenyl)acrylonitrile A preferred method of synthesis of (E)-2-(3-phenyl-n-propylaminocarbonyl)-3-(3-bromo-4,5-dihydroxyphenyl) acrylonitrile (Compound 3) is as follows:

1. A mixture of 0.69 g of 2.5 mM 5-iodovanillin, 0.5 g of N-3-phenyl-n-propyl cyanoacetamide and 50 mg β-alanine in 30 ml ethanol was refluxed for 5 hours. Evaporation gave an oil which was triturated with benzene-hexane and filtered to give 0.82 g of a bright yellow solid (71% yield) having a melting point of 83° C. Notably, the compound was observed to partially deteriorate over time when stored at room light. It is therefore preferred that the compound be stored as a solid and protected from light. The product gave the following analytical data: NMR (CDCl$_3$) δ 8.12 (1H,S), 7.75 (1H,d,J=2.0 Hz), 7.68 (1H,d,J=2.0 Hz), 7.30–7.10 (5H,m), 3.96 (3H,S,OCH$_3$), 3.45 (2H,q,J=6.0 Hz), 2.70 (2H, t, J=6.0 Hz), 1.95 (2H, quin, J=6.0 Hz). MS m/e 462 (M+,53), 357 (M—CH$_2$)$_3$Ph,18), 335 (M–I,100), 327(M–NH(CH$_2$)$_3$ Ph, 31).

2. 0.5 g of the compound of step 1 (3-methoxy-4-hydroxy-5-iodo α-cis cinnamone(3'phenylpropane) amide) and 0.4 ml of BBr$_3$ in 30 ml dichloromethane were then stirred at room temperature for 1.5 hours. Water was added and the reaction extracted with ethyl acetate. Evaporation and trituration with benzene-hexane gave 0.3 g of a light brown solid (63% yield) having a melting temperature of 184° C.

The product gave the following analytical data: NMR (acetone d$_6$) δ 8.01 (1H,S vinyl), 7.88 (1H,d,J=2.0 Hz), 7.66 (1H,d,J=2.0 Hz), 7.30 (5H,m,Ph), 3.42 (2H,t,J=6.0 Hz), 2.70 (2H,t,J=6.0 Hz), 1.96 (2H, quin., J=6.0 Hz). MS m/e 448 (M+, 3%), 321 (M–I,8), 217 (21), 201 (33), 118 (100), m/e.

5.4. Synthesis Of (E)-2-|(3-amino-4-cyano)pyrazo-5-yl]-3-(3,5-di-t-butyl-4-hydroxyphenyl)acrylonitrile A preferred method of synthesis of (E)-2-[(3-amino-4-cyano)pyrazo-5-yl]-3-(3,5-di-t-butyl-4-hydroxyphenyl) acrylonitrile (Compound 4) is as follows: A mixture of 0.7 g of 3,5-di-t-butyl-4-hydroxybenzaldehyde, 0.46 g of 3-amino-4-cyano-5-cyanomethyl pyrazole (prepared according to Carboni et al., 1958, *J. Chem. Soc.*, 80:2838) and 40 mg of β-alanine was refluxed for 15 hours. Cooling and filtering gave 0.5 g (46% yield) of yellow solid having a melting point of 255° C.

The product gave the following analytical data: NMR (CDCl$_3$) δ 7.92 (1H,S,vinyl), 7.80 (2H,S), 5.76 (1H,S,OH), 3.75 (2H,Br,S,NH$_2$), 1.48 (18H,S). MS m/e 364(M+1,28), 363 (M+,100%), 348 (M—CH$_3$,58%), 292 (M–56-CH$_3$/31%), 147 (41%), m/e.

5.5. Synthesis Of (E)-2-(3-phenyl-n-propylaminocarbonyl)-3-(3-isopropyl-4-hydroxy-5-(2-propylphenyl)acrylonitrile A preferred method of synthesis of (E)-2-(3-phenyl-n-propylaminocarbonyl)-3-(3-isopropyl-4-hydroxy-5-(2-propylphenyl)acrylonitrile (Compound 5) is as follows: A mixture of 0.4 g of 3,5-diisopropyl-6-hydroxy-benzaldehyde (for synthesis protocol, see Section 5.11 (step 2)), 0.55 g of N-3-phenyl-n-propyl cyanoacetamide (synthesized according to the protocol set forth in Gazit, et al., 1991, *J. Med. Chem.* 34(6):1896–1907) and 40 mg of β-alanine (in 20 ml ethanol) was refluxed for 5 hours. Workup (H$_2$O, HCl, dichloromethane) gave an oil which crystallized on standing. Trituration with benzene-hexane gave 0.4 g light yellow solid having a melting point of 120° C. Another 0.55 g of solid was obtained from the from the mother liquid. The overall yield was 65%.

The product gave the following analytical data: NMR (CDCl$_3$) δ 8.24(1H,S,vinyl), 7.73(2H,S), 7.23(5H,m), 5.50 (1H,S,OH), 3.46(2H,q,J=6.7 Hz, NH—CH$_2$), 3.17(2H, Septet, J=7.0 Hz), 2.71(2H,t,J=6.7 Hz), 1.95(2H, quintet, J=6.7 Hz), 1.30(12H,d,J=7.0 Hz).

5.6. Synthesis Of (E)-2-(benzylaminocarbonyl)-3-(3-iodo-4,5-dihydroxyphenyl)acrylonitrile A preferred method of synthesis of (E)-2-(benzylaminocarbonyl)-3-(3-iodo-4,5-dihydroxyphenyl) acrylonitrile (Compound 6) is as follows: A mixture of 0.4 g of 2-cyano-3-(4-hydroxy-3-iodo-5-methoxy) phenylacrylonitrile (which was prepared by condensation of 4-hydroxy-3-iodo-5-methoxybenzaldehyde with N-benzylcyanoacetamide) and 0.5 ml of BBr$_3$ in 20 ml dichloromethane was stirred for 2 hours at room temperature. Workup (H$_2$O, ethyl acetate) gave 0.16 g of a yellow solid (41 yield) having a melting point of 220° C.

The product gave the following analytical data: NMR (acetone-d$_6$) δ 8.05(1H,S,vinyl), 7.85(1H,d,J=2.1 Hz), 7.70 (1H,d,J=2.1 Hz), 7.30(5H,in), 4.6(2H,S).

5.7. Synthesis Of (E,E)-2-||2-||1-cyano-2(3,4-dihydroxyphenyl)ethenyl|carbonylamino|ethyl| aminocarbonyl-3-(3,4-dihydroxyphenyl)acrylonitrile A preferred method of synthesis of (E,E)-2-||2-|| 1-cyano-2(3,4-dihydroxyphenyl)ethenyl|carbonylamino|ethyl| aminocarbonyl]-3-(3,4-dihydroxyphenyl)acrylonitrile (Compound 7) is as follows: A mixture of 0.7 g of 3,4-dihydroxy benzaldehyde, 0.5 g of N-(cyanomethylcarbonylamino-n-propyl)cyanoacetamide and 4 drops piperidine in 20 ml ethanol was refluxed for 4 hours. Water was added. Extraction with ethyl acetate, evaporation and trituration with ethanol-dichloromethane gave 0.34 g (32% yield) of a yellow solid, having a melting point of 277° C.

5.8. Synthesis Of (E,E)-2-||4-||1-cyano-2-(3,4-dihydroxyphenyl)ethenyl|carbonylamino|-n-butyl| aminocarbonyl]-3-(3,4-dihydroxyphenyl)acrylonitrile A preferred method of synthesis of (E,E)-2-||4-|| 1-cyano-2-(3,4-dihydroxyphenyl)ethenyl|carbonylamino|-n-butyl| aminocarbonyl]-3-(3,4-dihydroxyphenyl)acrylonitrile (Compound 8) is as follows: The compound was prepared according to the protocol prescribed for the synthesis of compound above (Section 5.7, above). Following this protocol, a yellow solid (86% yield) resulted having a melting point of 283° C.

The product gave the following analytical data: NMR (acetone-d$_6$) δ 8.25 (1H,S,vinyl), 7.23 (2H,S, H2,6).

5.9. Synthesis Of (E,E)-|2-[2-cyano-2-(3,4-dihydroxyphenylcarbonyl)ethenyl|sulfonyl]-3-(3,4-dihydroxyphenyl)acrylonitrile A preferred method of synthesis of (E,E)-|2-[2-cyano-2-(3,4-dihydroxyphenylcarbonyl)ethenyl]sulfonyl]-3-(3,4-dihydroxyphenyl)acrylonitrile (Compound 9) is as follows: A mixture of 0.3 g of N-(2-cyanomethylcarbonylaminoethyl)cyanoacetamide and 0.55 g of 3,4-dihydroxy benzaldehyde with 30 mg β-alanine in 30 ml ethanol was refluxed for 6 hours and worked up. Evaporation of the ethyl acetate and trituration with acetone-benzene gave a 0.45 g (58% yield) of a yellow solid, having a melting point of 264° C. (stains hands).

The product gave the following analytical data: MS m/e 312 (28%), 265 (24), 211 (100%), 185 (15%), 161 (44%), 160 (M-(compound structure), 80%), 157(35), 129 (22), 114 (43) m/e. NMR (acetone-d$_6$) δ 8.15 (2H,s,vinyl), 7.77 (2H, d,J=2.3 Hz, H2), 7.59 (2H,dd,J=8.4, 2.3 Hz, H6), 7.07 (2H,d,J=8.4 Hz, H5).

5.10. Synthesis Of (E)-3-(indol-5-yl)-2-(3,4-dihydroxyphenyl carbonyl)acrylonitrile A preferred method of synthesis of (E)-3-(indol-5-yl)-2-(3,4-dihydroxyphenylcarbonyl)acrylonitrile (Compound 10) is as follows: A mixture of 130 mg of 5-formyl indole, 180 mg of cyanomethyl-(3,4-dihydroxyphenyl)ketone (prepared according to the protocol set forth at Gazit, et al., 1991, *J. Med. Chem.* 34:1896–1907) and 30 mg β-alanine was refluxed for 3 hours. Water was then added and the reaction extracted with ethyl acetate to give an oily solid containing some aldehyde. Chromatography gave 86 mg of a pure orange solid (28% yield) having a melting point of 185° C.

The product gave the following analytical data: MS m/e 304 (M+, 8%), 177 (29), 137 (C$_6$H$_3$(OH)$_2$CO$^+$, 100), 117 (12), 116 (indole+,15), 109 (93). NMR (acetone-d$_6$) δ 8.40 (1H,d,J=1.6 Hz, H$_4$), 8.18 (1H,S,vinyl), 8.03 (1H,dd,J=8.6, 1.6 Hz, H6), 7.63 (1H,d,J=8.6 Hz, H5), 7.54–7.40 (3H,m, H3+H2.6), 7.0 (1H,d J=8.6 Hz, HS), 6.69 (1H, d J=3.2 Hz,H2).

5.11. Synthesis Of (E)-2-|3-phenyl-n-propylaminothiocarbonyl|-3-(3,5-diisopropyl-4-hydroxyphenyl)acrylonitrile A preferred method of synthesis of (E)-2-|3-phenyl-n-propylaminothiocarbonyl|-3-(3,5-diisopropyl-4-hydroxyphenyl)acrylonitrile (Compound 11) is as follows:

1. A mixture of 6.2 g of N-phenylpropylcyanoacetamide (synthesized according to the protocol set forth at Gazit, et al., 1991, *J. Med. Chem.* 34(6):1896–1907) and 15 g Lawsson reagent in 60 ml toluene was refluxed for 3 hours. Chromatography resulted in 1.5 g (22% yield) of N-phenylpropylcyanothioacetamide as a red solid. The product gave the following analytical data: NMR (CDCl$_3$) δ 7.3 (5H,m), 3.81 (2H,S), 3.71 (2H,q, J=7.0 Hz), 2.74 (2H,t, J-7.0 Hz), 2.05 (2H, quintet, J-7.0 Hz).

2. A mixture of 18 g of 2,6-diisopropyl phenol and 1.8 g of hexamethylenetriamine (HMTA) in 60 ml trifluoroacetic acid (TFA) was refluxed for 3.5 hours. Workup, chromatography and trituration with hexane gave 5.3 g (26% yield) of 3,8-diisopropyl-6-hydroxybenzaldehyde white solid, having a melting point of 103° C. Analytical analysis of the product gave the following data: NMR (CDCl$_3$) δ 9.87(1H,S,CHO), 7.63(2H,S), 3.19(2H,septet,J=7.7 Hz), 1.30(12H,d,J= 7.7 Hz).

3. 0.6 g of the compound of Step 1 (N-phenylpropyl cyanothioacetamide), 0.6 g of the compound of Step 2 and 40 mg β-alanine in 40 ml ethanol were refluxed for 4 hours. Evaporation and chromatography gave 0.6 g (50% yield) of Compound 11 as a viscous oil. NMR (CDCl$_3$) δ 8.76(1H,S,vinyl) , 7.78(2H,S,H2.6), 7.25 (5H,m), 5.60(1H,S,OH), 3.90(2H,q,J=7.0 Hz), 3.17 (2H,Septet, J=7.0 Hz), 2.76(2H,t,J=7.0 Hz), 2.11(2H, quintet, J=7.0 Hz), 1.29(12H,d,J=7.0 Hz). MS m/e 407 (M+1, 55), 406 (M+, 70), 373(M–CH$_3$–H$_2$O,100), 363 (M-isopropyl, 72), 272(M–NH(CH$_2$)$_3$ Ph, 20), 259 (58), 230 (28), 91 (28).

5.12. Synthesis Of (E)-2-[1-cyano-2-(5-bromo-3,4-dihydroxyphenyl)ethenylsulfonyl]-3-(3-bromo-4,5-dihydroxy phenyl)acrylonitrile A preferred method of synthesis of (E)-2-[1-cyano-2-(5-bromo-3,4-dihydroxyphenyl)ethenylsulfonyl]-3-(3-bromo-4,5-dihydroxyphenyl)acrylonitrile (Compound 12) is as follows: 10 ml of ethanol containing 230 mg of 5-bromo 3,4-dihydroxy benzaledehyde, 76 mg of diacetonitrile sulphone and 10 mg of β-alanine were refluxed for 5 hours. Cooling and filtering gave 220 mg (76% yield) of an orange solid having a melting point greater that 300° C.

The product gave the following analytical data: NMR (acetone-d$_6$) δ 8.18(2H,S,vinyl), 7.90 (2H,d,J=1.6 Hz), 7.78 (2H,d,J=1.6 Hz).

5.13. Synthesis Of 2-[(4-iodophenyl)amino]-6,7-dimethyl quinoxaline

A preferred method of synthesis of 2-[(4-iodophenyl) amino]-6,7-dimethyl quinoxaline (Compound 13) is as follows:

1. A mixture of 2 g of 4,5-dimethyl-1,2-diaminobenzene and 1.5 g of glyoxalic acid hydrate in 30 ml ethanol was refluxed for 2 hours. Cooling and filtering gave 1.2 g (46% yield) of a white solid, having a melting point of 263° C. The product gave the following analytical data: NMR (DMSO d$_6$) δ 60:40 mixture.
major—8.07 (1H,S), 7.55(1H,S), 7.06(1H,S), 2.30(6H,S).
minor—8.02 (1H,S), 7.42(1H,S), 7.28(1H,S), 2.28(6H,S).

2. A mixture of 1.1 g of the product of step 1 (6,7-dimethylquinoxalone), 1 ml phosphrous oxychloride (POCl$_3$) and 1 ml dimethyl aniline in 20 ml toluene were refluxed for 2 hours. Workup (NH$_3$, dichloromethane) and chromatography gave 0.4 g (33% yield) of a white solid (2-chloro-6,7-dimethylquinoxaline), having a melting point 86° C. The product gave the following analytical data: NMR (CDCl$_3$) δ 8.68(1H,S,H$_2$), 7.85(1H,S), 7.76 (1H,S), 2.50(6H,S).

3. A mixture of 210 mg of the product of step 2 (2-chloro-6,7-dimethylquinoxaline) and 0.8 g of p-iodoaniline was heated in 10 ml ethanol at 100° C. for 4 hours. Chromatography gave 245 mg (60% yield) of a light green solid having a melting point of 228° C.

The product gave the following analytical data: NMR (CDCl$_3$) δ 8.32(1H,S), 7.67(1H,S), 7.64(1H,S), 7.68, 7.56 (4H,Abq, JAB=9.0 Hz).

5.14. Synthesis Of 2-(3,4-dihydroxyphenyl)-6,7-dimethylquinoxaline

A method of synthesis of 2-(3,4-dihydroxyphenyl)-6,7-dimethyl-quinoxaline (Compound 14) is as follows: 1.4 g of 4,5-dimethyl 1,2-phenylenediamine and 1.9 g of α-chloro 3,4-dihydroxy acetophenone in 15 ml dimethylsulfoxide were heated for 1.5 hours at 100° C. 80 ml of H$_2$O was added and the suspension was left overnight at room temperature and filtered to give 2.5 g (67% yield) of a brown solid.

The product gave the following analytical data: NMR (acetone-d$_6$) δ 9.28(1H,S,H2), 8.40(Br.S,OH) 7.89(1H,d,J= 2.2 Hz, H2'), 7.82 (2H,S,H55,8), 7.72(1H,dd,J=8.3,2.2 Hz,H6'), 7.02 (1H,d,J=8.3 Hz,H5'), 2.52 (6H,S,CH$_3$). DMSO d6 9.30(1H,S,H2), 7.81(2H,S,H5,8), 7.75 (1H,d,J= 2.2 Hz,H$_2$'), 7.62(1H,dd,J=8.3,2.2 Hz,H6'), 6.90 (1H,d,J=8.3 Hz, H5'), 2.44(6H,S,CH$_3$)

A second method of synthesis of 2-(3,4-dihydroxy) phenyl-6,7-dimethyl-quinoxaline is as follows: 1 g and 1.9 g of the above reagents in 25 ml ethanol were refluxed 2 hours. Cooling and filtering gave 0.76 g (18% yield) of a deep yellow solid having a melting point of 278° C. as the HCl salt.

5.15. Synthesis Of 4-(4-iodophenylamino)-6,7-dimethoxy quinazoline

A preferred method of synthesis of the compound (Compound 15) is as follows:

1. A mixture of 7 g of 4,5-dimethoxy 2-aminobenzoic acid and 8 ml of formamide was heated for 2 hours at 170° C. Cold water was added and the solid filtered to give 0.9 g (12% yield) of a light-brown solid (6,7-dimethoxyquinazolone), having a melting point of 308° C.

The product gave the following analytical data: NMR (DMSO-d$_6$) δ 8.0(1H,S), 7.43(1H,S), 7.12(1H,S), 3.89(3H, S), 3.85(3H,S).

2. 0.8 g of the compound of Step 1, 1 ml POCl$_3$ and 1 ml dimethylaniline in 20 ml toluene were refluxed for 3.5 hours. Workup and trituration with hexane gave 0.5 g of a light grey solid (57% yield), having a melting point of 188° C.

The product gave the following analytical data: NMR (CDCl$_3$) δ 8.88(1H,S), 7.41(1H,S), 7.36(1H,S), 4.09(3H,S), 4.08(3H,S).

3. A mixture of 300 mg of 4-chloro-6,7-dimethoxyquinazoline and 300 mg of 3-iodoaniline in 10 ml ethanol was refluxed for 1 hour. Cooling and filtering gave 540 mg (93% yield) of a white solid as the HCl salt. The solid had a melting point of 278° C.

The product gave the following analytical data: NMR (DMSO-$d_6$) δ 8.87(1H,S,H2), 8.27(1H,S), 8.13(1H,S), 7.8–7.66(2H,m), 7.33(2H,m), 4.02(3H,S), 4.0(3H,S).

5.16. Synthesis Of 4-(3-hyrdroxyphenylamino)-6-methylquinazoline

A preferred method of synthesis of 4-(3-hydroxyphenylamino)-6-methylquinazoline (Compound 16) is as follows:

1. A mixture of 0.8 g of 5-methyl-2-aminobenzoic acid and 15 ml formamide was heated at 170° C. for 1.5 hours. Water was added and the solid filtered to give 7.3 g (83% yield) of a brown-white solid (6-methylquinazolone) having a melting point of 268° C.

2. A mixture of 5 g of the compound of step 1, 5 ml of POCl$_3$ and 5 ml dimethyl aniline in 40 ml toluene were refluxed for 3.5 hours. Workup (NH$_3$, H$_2$O, ethyl acetate) gave a dark solid. Chromatography yielded (29% yield) 1.61 g of a white solid (4-chloro-6-methylquinazoline) having a melting point of 98° C.

The product gave the following analytical data: NMR (CDCl$_3$) δ 9.0 (1H,S,H2), 8.04(1H,d,J=2.0 Hz,H$_5$), 7.96(1H, d,J=8.8 Hz,H$_8$), 7.80(1H,dd,J=8.8,2.0 Hz, H$_7$), 2.62(3H,S).

3. A mixture of 230 mg of the compound of step 2 and 145 mg of m-aminophenol in 10 ml ethanol was refluxed for 50 minutes. Cooling and filtering gave 300 mg (80% yield) of a light yellow solid, as the HCl salt. The product had a melting point of 262° C.

The product gave the following analytical data: (DMSO-$d_6$) δ 8.89(1H,S,H2), 8.72 (1H,S,H5), 7.90(2H,ABq,J=8.0 Hz, H7,8), 7.2(3H,m), 6.75(1H,m), 2.55(3,H,S).

5.17. Synthesis Of 2-(3,4-dichlorophenylamino)-6,7-dimethylquinoxaline

A preferred method of synthesis of 2-(3,4-dichlorophenylamino)-6,7-dimethylquinoxaline (Compound 17) is as follows: A mixture of 150 mg of the compound of 2-chloro-6,7-dimethylquinoxaline (which may be synthesized according to the protocol at Section 5.13 (step 2)) and 0.7 g of 3,4-dichloroaniline was heated at 100° C. for 3.5 hours. Chromatography gave 80 mg (33% yield) of a yellow brown solid, having a melting point of 229° C.

The product gave the following analytical data: NMR (CDCl$_3$) δ 8.32(1H,S), 8.16(1H,d,J=2.4 Hz,H2'), 7.71(1H, Br.S), 7.65(1H,Br.S), 7.57(1H,dd,J=2.4, 9.2 Hz, H6'), 7.43 (1H,d,J=9.2 Hz, H5'), 2.48(3H,S), 2.46(3H,S)

5.18. Synthesis Of 4-(3-hydroxyphenylamino)-quinazoline

A preferred method of synthesis of 4-(3-hydroxyphenylamino)-quinazoline (Compound 18) is as follows:

1. A mixture of 4.6 g of quinazolone, 5 ml of POCl$_3$ and 5 ml of dimethylaniline in 50 ml toluene was refluxed for 3.5 hours. Workup (NH$_3$, H$_2$O and ethylacetate) yielded a green oil. Chromotography resulted in a light brown solid. Sublimation at 160° C. (11 mm Hg) gave 1.48 g (29% yield) of a white solid (4-chloro-quinazoline) having a melting point of 72° C. This product gave the following analytical data: NMR (CDCl$_3$) δ 9.05 (1H,S), 8.27 (1H,m), 8.1–7.9 (2H,m) 7.75 (1H,m).

2. A mixture of 0.37 g of the compound of step 1 and 0.24 g of m-hydroxyaniline in 10 ml ethanol was refluxed for 1 hour. Cooling and filtering gave 0.25 g (41% yield) of a light-yellow solid as the HCl salt. The solid turns light green on standing overnight. The product has melting point of 268° C.

The product gave the following analytical data: NMR (DMSO-$d_6$) δ 8.99 (1H,S), 8.93(2H,S), 8.15–7.81 (3H,m), 7.31–7.12(3H,m), 6.77(1H,d,J=7.4 Hz).

5.19. Synthesis Of 2-(n-propylamino)-3-chloroquinoxaline

A preferred method of synthesis of 2-(n-propylamino)-3-chloroquinoxaline (Compound 19) is as follows: 0.8 g of 2-phenyl-3,6,7-trimethyl quinoxaline 10 ml dimethylsulfoxide was heated for 40 minutes at 90° C. Workup and chromatography gave 40 mg (4% yield) of a white solid having a melting point of 148° C. The product gave the following analytical data: NMR (CDCl$_3$) δ 8.03(1H,S), 7.90(1H,S), 7.60(5H,m), 6.96 (1H, S, CHBr$_2$), 2.52 (6H, S).

Following the same protocol, 0.3 g (47% yield) of a white solid was obtained having a melting point of 150° C. The product gave the following analytical data: NMR(CDCl$_3$) δ 11.30(1H,S,CHO), 8.05(1H,S), 7.96(1H,S), 7.67(2H,m), 7.55(3H,m), 2.55(6H,5).

5.20. Synthesis Of 4-[(4-methylphenyl)mercapto]quinazoline

A preferred method of synthesis of the compound (Compound 20) is as follows: A mixture of 250 mg of 4-chloro-6-methyl-quinazoline, 180 mg of p-thiocresole and 100 mg of potassium hydroxide (KOH) are combined in 20 ml CH$_3$CN and stirred 24 hours at room temperature. Workup (H$_2$O, dichloromethane) and trituration with hexane gave 40 mg (10% yield) of a light blue solid having a melting point of 96° C.

The product gave the following analytical results: NMR (CDCl3) δ 8.81(1H,S), 7.96(1H,d,J=2.0 Hz,H5), 7.85(1H, d,J=9.0 Hz, H8), 7.68(1H,dd,J=9.0, 2.0 Hz, H7), 7.51, 7.30(4H,ABq,JAB=8.2 Hz), 2.56(3H,S), 2.42(3H,S). MS m/e 266 (M+,40%), 265 (M−1,100%) m/e.

5.21. Synthesis Of 2-chloro-4-(3-chlorophenylamino)-6,7-dimethoxyquinazoline A preferred method of synthesis of 2-chloro-4-(3-chlorophenylamino)-6,7-dimethoxyquinazoline (Compound 21) is as follows:

1. A mixture of 8 g of 6,7-dimethoxy-2,4-quinazolinedione, 23 ml of POCl$_3$ and 10 ml of dimethylaniline in 30 ml toluene Was refluxed for 5 hours. Workup (H$_2$O, NH$_3$, dichloromethane) and titration with hexane gave 7 g (75% yield) of a light green solid (2,4-dichloro-6,7-dimethyoxy-quinazoline having a melting temperature of 156° C. The product gave the following analytical results: NMR (CDCl$_3$) δ 7.36(1H, S), 7.28(1H,S), 4.07(3H,S), 4.06(3H,S).

2. A mixture of 2.6 g of the compound of step 1 and 1.3 g of m-chloroaniline in 20 ml ethanol was refluxed for 1 hour. The mixture was then cooled and filtered to give 3.5 g (90% yield) pink-white solid.

Alternatively, a second method of synthesis using the free base was used. 3.4 g of the material form above was treated with NH$_3$—H$_2$O and extracted with ethyl acetate. Recrystallization from benzene-hexane gave 2.3 g (74% yield) of a white solid having a melting point of 222° C.

The product gave the following analytical data: NMR (CDCl$_3$) δ 7.74(1H,t,J=2.2 Hz,H2'), 7.63(1H,m), 7.30(1H, m), 7.16(1H,S), 7.12(1H,m), 6.98(1H,t,J=8.0 Hz), 4.0(3H, S), 3.97(3H,S).

5.22. Synthesis Of (Z)-1-(2-chlorophenyl)-2-[2,2-dicyanoethenyl]hydrazine

A preferred method of synthesis of (Z)-1-(2-chlorophenyl)-2-[2,2-dicyanoethenyl]hydrazine (Compound 22) is as follows: 2.4 g of sodium nitrite (NaNO$_2$) was added to 4 g of m-chloro-aniline in 20 ml of diluted hydrochloric acid and 20 ml H₂O and then cooled in ice for approximately 0.5 hours. The mixture was then added into a solution of 2.2 g malononitrile and 10 g potassium acetate in 100 ml ethanol. After 0.5 hours in the cold and 1 hour at room temperature the solid was filtered, washed with water and dried to give 2.4 g (37% yield) yellow solid.

The product gave the following analytical data: mp-170° C. NMR (CDCl₃) δ 7.4–7.2, m.

5.23. Synthesis Of 2-phenyl-1,4-diazaanthracene

A preferred method of synthesis of 2-phenyl-1,4-diazaanthracene (Compound 23) is as follows: 20 ml of ethanol containing 0.47 grams; of 2,3-diaminonaphthalene and 0.47 grams of phenyl gloxal hydrate were refluxed for 1.5 hour. Cooling and filtering gave 0.5 g (65%) of a light brown solid with a melting point of 163° C.

The product gave the following analytical data: NMR (CDCl₃): δ 9.38 (1H, 1.c., H2), 8.71, 8.67 (2H, 2d, H5,10), 8.25, 8.10 (4H, AA'BB'm, H6-9), 7.58(5H, m, Ph). MS m/e 256(M+, 100%), 229 (M–CN, 12%), 126(71%) m/e.

5.24. Synthesis Of N-(2,5-dihydroxylbenzyl)-4-methoxycarbonyl aniline

A preferred method of synthesis of N-(2,5-dihydroxylbenzyl)-4-methoxycarbonylaniline (Compound 24) is as follows: 0.7 g of 2,5-dihydroxybenzaldehyde and 0.75 g of 3-aminomethylbenzoate in 40 ml of methanol were refluxed for 3 hours and cooled. 0.5 g of sodiumcyanoborohydride (NaCNBH₄) was then added. After 12 hours at room temperature, workup (H₂O, ethylacetate), and chromatography (silica gel, elution with 5% CH₃OH in dichloromethane), 0.42 g (31% yield) of a light yellow solid was obtained.

The product gave the following analytical data: mp 175° C. NMR (acetone-d₆) δ 7.78, 6.68 (4H, ABq, JAB=8.8 Hz), 6.74 (1H,d,J=3.0 Hz, H6), 6.72 (1H,d,J=8.5 Hz,H3), 6.55 (1H,d,J=8.5,3.0 Hz,H₄), 4.34 (2H,s,CH₂N), 3.76 (3H,s, COOCH₃).

5.25. Synthesis Of N-(2-chlorophenyl)-2-cyano-2-(N-3-trifluorophenylaminocarbonyl)-thioacetamide N-(2-chlorophenyl)-2-cyano-2-(N-3-trifluorophenylamino-carbonyl)-thioacetamide (Compound 25) may be synthesized as follows:

680 mg of sodium ethoxide was added to a solution of 1.6 gram of N-3-trifluoromethylphenyl cyanoacetamide in 20 ml of tetrahycdrofuran at 0° C. This mixture was stirred at 0° C. for 1 hour and 1.7 g of 2-chlorophenylisothiocyanate in 5 ml of tetrahydrofuran was added dropwise. After addition, the mixture was warmed to room temperature and heated at 50° C. for 6 hours. Upon cooling, all the ethanol was removed and the resulting solid was resuspended in 10 ml of water. This was then added to 15 ml of 0.3M sodium hydroxide solution, shaken vigorously and washed in 50 ml of ethyl ether. The aqueous layer was then acidified with 1N hydrochloric acid to pH 1. The solid was then collected by suction filtration to produce 630 mg of N-2-chlorophenyl(2-cyano-2-N-3-trifluorophenylaminocarbonyl) thioacetamide.

5.26. Synthesis Of (E)-2-cyanomethylsufonyl-3-(3-bromo-4,5-dihydroxyphenyl)acrylonitrile A preferred method of synthesis of (E)-2-cyanomethylsufonyl-3-(3-bromo-4,5-dihydroxyphenyl)acrylonitrile (Compound 26) is as follows: A mixture of 500 mg of 5-bromo,3,4-dihydroxybenzaldehyde and 700 mg of sulfonyldiacetonitrile in 6 ml of ethanol was refluxed with a few drops of piperidine for 4 hours. Ethanol was removed in a rotavap and the mixture worked up with ethyl acetate, diluted acid and brine. A portion of the crude was then purified by HPLC on a C-18 column to provide about 50 mg of (E)-2-cyanomethylsufonyl-3-(3-bromo-4,5-dihydroxyphenyl)acrylonitrile.

5.27. Synthesis Of (1-benzyl-2-hydroxyphenyl)pyrolido|3,4-b|3,4-dihydro-4-oxoquinazoline A preferred method of synthesis of (1-benzyl-2-hydroxyphenyl)pyrolido|3,4-b|3,4-dihydro-4-oxoquinazoline (Compound 27) is as follows: 0.01 mol (1.07 g) of benzylamine and 0.01 mol (1.22 g) of 4-hydroxybenzaldehyde were mixed together in 15 ml of ethanol and refluxed on a waterbath, for 15 minutes. 0.01 mol (3.44 g) of 2-(1'-tosyloxyethyl)-quinazolin-4-one and one drop of pyridine were added and the mixture was refluxed for six hours. The resulting solution was evaporated and extracted with a 5% water solution of sodium bicarbonate. The remaining crystals were filtered off, washed with water and recrystallized from isopropanol. 3.40 g of compound as obtained (89% yield) having a melting point of 217–219° C.

The product (C₂₄H₂₁N₃O₂) gave the following analytical data:

Elemental analysis |%| of Product Calculated: C: 75.18 H: 5.52 N: 10.96 Found: C: 75.26 H: 5.47 N: 10.88

5.28. Synthesis Of 2-(3-chlorophenylamino)-6,7-dimethylquinoxaline

A preferred method of synthesis of 2-(3-chlorophenylamino)-6,7-dimethylquinoxaline (Compound 28) is as follows: 200 mg of 2-chloro-6,7-dimethylquinoxaline and 700 mg m-chloro aniline were heated without solvent at 100° C. for 2.5 hours. Chromatography gave 100 mg of a white solid (34% yield) having a melting point of 175° C.

The product gave the following data: NMR (CDCl₃) δ 8.33(1H,S), 7.97(1H,m), 7.68(1H,S), 7.62(1H,S), 7.54(1H, m), 7.27(1H,m), 7.05(1H,m), 2.45(3H,S), 2.43(3H,S). MS m/e 285, 283(M+,29,81%), 248(m-Cl,7).

5.29. Synthesis Of (E)-2-(3,4-dihydroxybenzoyl)-3-dihydroxyphenyl)acrylonitrile A preferred method of synthesis of (E)-2-(3,4-dihydroxybenzoyl)-3-dihydroxyphenyl)acrylonitrile (Compound 29) is as follows: Solid potassium cyanide (KCN) (3 g, 46 mmol) was added to 2-chloro-3',4'-dihydroxyacetophenone (6 g) in 30 ml of dimethylsulfoxide. The reaction mixture was stirred at 100° C. for 2.5 hours. After cooling, 100 ml of 1N hydrochloric acid was added, and the reaction mixture was extracted with ethyl acetate. Drying and evaporation gave a red oily solid which was purified by chromatography on silica gel. The first fractions eluted with 3% methanol in dichloromethane were evaporated and triturated with dichloromethane. Filtering gave 1 g (18% yield) of a light yellow solid having a melting point of 217° C.

The product gave the following analytical data: NMR (acetone-d6) δ 7.51(2H,m,H2,6), 6.97 (1H,d,J=8.0 Hz, H5), 4.43 (2H,s,CH₂CN).

5.30. Synthesis Of 2-(4-bromophenylamino)-6,7-quinoxaline

A preferred method of synthesis of 2-(4-bromophenylamino)-6,7-quinoxaline (Compound 30) is as follows: 200 mg of 2-chloro-6,7-dimethyl quinoxaline (synthesized according to the protocol at Section 5.13, step 2) and 0.8 g of p-bromoaniline were heated at 100° for 3.5 hours. Chromatography gave 25 mg (37% yield) of a light yellow solid, having a melting point of 235° C.

The product gave the following analytical data: NMR (CDCl₃) δ 8.32(1H,S), 7.68(1H,S), 7.60(1H,Br.S), 7.68, 7.48(4H,ABq, JAB=8.8 Hz), 2.45(3H,S), 2.43(3H,S).

6. EXAMPLE: ELISA Assay To Measure Kinase Activity Of FLK-1 Receptor In FLK-1/NIH Cells An ELISA assay was conducted to measure the kinase activity of the FLK-1 receptor and more specifically, the inhibition or activiation of protein tyrosine kinase activity on the FLK-1 receptor.

6.1. Materials And Methods

Materials.

The following reagents and supplies were used:
a. Corning 96-well ELISA plates (Corning Catalog No. 25805-96);
b. Cappel Goat anti-rabbit IgG (catalog no. 55641);
c. PBS (Gibco Catalog No. 450-1300EB);
d. TBSW Buffer (50 mM Tris (pH 7.2)m 150 mM NaCl and 0.1% Tween-20);
e. Ethanolamine stock (10% ethanolamine (pH 7.0), stored at 4° C.);
f. HNTG buffer (20 mM HEPES buffer (pH 7.5), 150 mM NaCl, 0.2% Triton X-100, and 10% Glycerol);
g. EDTA (0.5M (pH 7.0) as a 100×stock);
h. Sodium Ortho Vanadate (0.5M as a 100×stock);
i. Sodium pyro phosphate (0.2M as a 100×stock);
j. NUNC 96 well V bottom polypropylene plates (Applied Scientific Catalog No. AS-72092);
k. NIH3T3C7#3 Cells (FLK-1 infected cells)
l. DMEM with 1×high glucose L Gulatamine (catalog No. 11965-050);
m. FBS, Gibco (catalog no. 16000-028);
n. L-glutamine, Gibco (catalog no. 25030-016);
o. VEGF, PeproTech, Inc. (catalog no. 100-20) (kept as 1 ug/100 ul stock in Milli-Q $dH_2O$ and stored at $-20°$ C.;
p. Affinity purified anti-flk-1 antiserum, Enzymology Lab, Sugen, Inc.;
q. UB40 monoclonal antibody specific for phophotyrosine, Enzymology Lab, Sugen, Inc.;
r. EIA grade Goat anti-mouse IgG-POD (BioRad catalog no. 172-1011);
s. 2,2-azino-bis(3-ethylbenz-thiazoline-6-sulfonic acid (ABTS) solution (100 mM citric acid (anhydrous), 250 mM $Na_2HPO_4$ (pH 4.0), 0.5 mg/ml ABTS (Sigma catalog no. A-1888)), solution should be stored in dark at 4° C. until ready for use;
t. $H_2O_2$ (30% solution) (Fisher catalog no. H325)
u. $ABTS/H_2O_2$ (15 ml ABTS solution, 2 ul $H_2O_2$) prepared 5 minutes before use and left at room temperature;
v. 0.2M HCl stock in $H_2O$;
w. dimethylsulfoxide (100%) (Sigma Catalog No. D-8418); and
y. Trypsin-EDTA (Gibco BRL Catalog No. 25200-049).

Protocol.

The following protocol was used to conduct the ELISA Assay:

1. Coat Corning 96-well elisa plates with 1.0 ug per well Cappel Anti-rabbit IgG antibody in 0.1M Na2CO3 pH 9.6. Bring final volume to 150 ul per well. Coat plates overnight at 4 C. Plates can be kept up to two weeks when stored at 4° C.
2. Grow cells in 30 ml of Growth media 9DMEM. 2.0 mM L-Glutamine, 10% FBS) until confluent in 150 cm tissue culture dishes at 37° C., 5% $CO_2$.
3. Harvest cells by tyrpsination and seed in Corning 25850 polystyrene 96-well roundbottom cell plates, 25,000 cells/well in 200 uL of growth media.
4. Grow cells at least one day at 37° C., 5% $CO_2$.
5. Wash cells with D-PBS 1×.
6. Add 200 ul/well of starvation media (DMEM, 2.0 mM 1-Glutamine, 0.1% FBS). Incubate overnight at 37° C., 5% $CO_2$.
7. Dilute Compounds/Extracts 1:20 in polyproplyene 96 well plates using starvation media. Dilute dimethylsulfoxide 1:20 for use in control wells.
8. Remove starvation media from 96 well cell culture plates and add 162 ul of fresh starvation media to each well.
9. Add 18ul of 1:20 diluted Compound/Extract dilution (from step #7) to each well plus the 1:20 dimethylsulfoxide dilution to the control wells (±VEGF), for a final dilution of 1:200 after cell stimulation. Final dimethylsulfoxide is 0.5%. Incubate the plate at 37° C., 5% $CO_2$ for two hours.
10. Remove unbound antibody from Elisa plates by inverting plate to remove liquid. Wash 3 times with TBSW+0.5% Ethanolamine, pH 7.0. Pat the plate on a paper towel to remove excess liquid and bubbles.
11. Block plates with TBSW+0.5% Ethanolamine, pH 7.0. 150 ul per well. Incubate plate thirty minutes while shaking on a microtiter plate shaker.
12. Wash plate 3 times as described in step 10.
13. Add 0.5ug/well affinity purified anti-flk-1 polyclonal rabbit antiserum. Bring final volume to 150 ul/well with TBSW+0.5% Ethanolamine pH 7.0. Incubate plate for thirty minutes while shaking.
14. Add 180 µl starvation medium to the cells and stimulate cells with 20 ul/well 10.0 mM Sodium Ortho Vanadate and 500 ng/ml VEGF (resulting in a final concentration of 1.0 mM Sodium Ortho Vanadate and 50 ng/ml VEGF per well) for eight minutes at 37° C., 5% $CO_2$. Negative control wells receive only starvation medium.
15. After eight minutes, media are removed from the cells and washed one time with 200 ul/well PBS.
16. Lyse cells in 150 ul/well HNTG while shaking at room temperature for five minutes. HNTG formulation includes sodium ortho vanadate, sodium pyro phosphate and EDTA.
17. Wash Elisa plate three times as described in step 10.
18. Transfer cell lysates from the cell plate to elisa plate and incubate while shaking for two hours. To transfer cell lysate pipette up and down while scrapping the wells.
19. Wash plate three times as described in step 10.
20. Incubate Elisa plate with 0.02 ug/well UB40 in TBSW+05% ethanolamine. Bring final volume to 150 ul/well. Incubate while shaking for 30 minutes.
21. Wash plate three times as described in step 10.
22. Incubate elisa plate with 1:10,000 diluted EIA grade Goat anti-mouse IgG conjugated horseradish peroxidase in TBSW+0.5% ethanolamine, pH 7.0. Bring final volume to 150 ul/well. Incubate while shaking for thirty minutes.
23. Wash plate as described in step 10.
24. Add 100 ul of ABTS/H202 solution to well. Incubate ten minutes while shaking.
25. Add 100 ul of 0.2M HCL for 0.1M HCL final to stop the color development reaction. Shake 1 minute at room temperature. Remove bubbles with slow stream of air and read the ELISA plate in an ELISA plate reader at 410 nm.

6.2. Experimental Results

The results obtained for the tested compounds of the present invention are set forth at Table 2.

TABLE 2

ELISA In Vitro Assay Results
FLK-1R ELISA ASSAY RESULTS

| Compound | IC50 (µM) | Compound | IC50 (µM) |
|---|---|---|---|
| 7 | 37.5 | 31 | 3.3 |
| 8 | 10.8 | 31 | 33.9 |
| 1 | 0.8 | 32 | 18.0 |
| 9 | 27.4 | 12 | 7.1 |
| 3 | 4.9 | 4 | 8.9 |
| 5 | 0.7 | 6 | 21.2 |
| 11 | 9.8 | 33 | 48.4 |
| 26 | 11 | 34 | 1.8 |
| 35 | 0.7 | 23 | 4.4 |
| 14 | 9.3 | 19 | 25.6 |
| 36 | 34.6 | 28 | 16.0 |
| 37 | 20.3 | 17 | 15.0 |
| 13 | 10.4 | 18 | 34.60 |
| 16 | 35.1 | 20 | 17.8 |
| 38 | 29.2 | 21 | 9.9 |
| 27 | 3.4 | 25 | 8.5 |
| 39 | 10 | 10 | 17.7 |
| 24 | 28.9 | 40 | 54.0 |
| 22 | 2.3 | 41 | >50 |
| 42 | >50 | 43 | >50 |
| 44 | >50 | 45 | >50 |
| 46 | >50 | 47 | ~50 |
| 48 | >50 | 49 | >50 |
| 50 | >50 | 51 | >50 |
| 52 | >50 | 53 | >50 |
| 54 | ~50 | 55 | >50 |
| 56 | >50 | 57 | 12.3 |
| 58 | >50 | 59 | >50 |
| 60 | 0.3 | 61 | >50 |
| 22 | 2.3 | 62 | >50 |
| 63 | 17.0 | 64 | 3.7 |
| 65 | 14.3 | | |

7. EXAMPLES: Effect Of Compounds In In Vivo Studies

The ability of one of the compounds of the present invention, leflunomide (Compound 40), to inhibit ovarian, melanoma, prostate, lung and mammary tumor cell lines established as SC xenografts was examined. These studies were conducted using doses ranging from 12 to 20 mg/kg/day.

7.1. Materials And Methods.

The tumor cells were implanted subcutaneously into the indicated strains of mice. Treatment was initiated on day 1 post implantation unless otherwise indicated (e.g. treatment of the SCID mouse related to the A375 melanoma cell line began on Day 9). Eight (8) to ten (10) mice comprised each test group.

Specifically

Animals.

Female athymic mice (BALB/c, nu/nu), BALB/c mice, Wistar rats and Fisher 344 rats were obtained from Simonsen Laboratories (Gilroy, Calif.). Female A/J mice were obtained from Jackson Laboratory (Bar Harbor, Me.). DA rats were obtained from B&K Universal, Inc. (Fremont, Calif.). Athymic R/Nu rats, DBA/2N mice, and BALB/c mice were obtained from Harlan Sprague Dawley (Indianapolis, Ind.). Female C57BL/6 mice were obtained from Taconic (Germantown, N.Y.). All animals were maintained under clean--room conditions in Micro-isolator cages with Alpha-dri bedding. They received sterile rodent chow and water ad libitum.

All procedures were conducted in accordance with the NIH Guide for the Care and Use Of Laboratory Animals.

Subcutaneous Xenograft Model.

Cell lines were grown in appropriate medium as described (See Section 6). Cells were harvested at or near confluency with 0.05% Trypsin-EDTA and pelleted at 450×g for 10 min. Pellets were resuspended in sterile PBS or media (without FBS) to a suitable concentration indicated in the Figure legends and the cells were implanted into the hindflank of mice. Tumor growth was measured over 3 to 6 weeks using venier calipers tumor volumes were calculated as a product of length×width×height unless otherwise indicated. P values were calculated using the Students' t-test. su101 in 50–100 uL excipient (dimethylsulfoxide, PBTE, PBTE6C:D5W, or PBTE:D5W) was delivered by IP injection at concentrations indicated in the Figure legends.

Intracerebral Xenograft Model.

For the mouse IC model, rat C6 glioma cells were harvested and suspended in sterile PBS at a concentration of $2.5 \times 10^7$ cells/ml and placed on ice. Cells were implanted into BALB/c, nu/nu mice in the following manner: the frontoparietal scalps of mice were shaved with animal clippers if necessary before swabbing with 70% ethanol. Animals were anesthetized with isofluorane and the needle was inserted through the skull into the left hemisphere of the brain. Cells were dispensed from Hamilton Gas-tight Syringes using 30 ga ½ inch needles fitted with sleeves that allowed only a 3 mm penetration. A repeater dispenser was used for accurate delivery of 4 uL of cell suspension. Animals were monitored daily for well-being and were sacrificed when they had a weight loss of about 40% and/or showed neurological symptoms.

For the rat IC model, rats (Wistar, Sprague Dawley, Fisher 344, or athymic R/Nu; approximately 200 g) were anesthetized by an IP injection of 100 mg/kg Ketaset (ketamine hydrochloride; Aveco, Fort Dodge, Iowa) and 5 mg/kg Rompun (xylazine, 2% solution; Bayer, Germany). After onset of anesthesia, the scalp was shaved and the animal was oriented in a stereotaxic apparatus (Stoelting, Wood Dale, Ill.). The skin at the incision site was cleaned 3 times with alternating swabs of 70% ethanol and 10% Poidone-Iodine. A median 1.0–1.5 cm incision was made in the scalp using a sterile surgical blade. The skin was detached slightly and pulled to the sides to expose the sutures on the skull surface. A dental drill (Stopiting, Wood Dale, Ill.) was used to make a small (1–2 mm diameter) burrhole in the skull approximately 1 mm anterior and 2 mm lateral to the bregma. The cell suspension was drawn into a 50 uL Hamilton syringe fitted with a 23 or 25 g a standard bevel needle. The syringe was oriented in the burrhole at the level of the arachnoidea and lowered until the tip of the needle was 3 mm deep into the brain structure, where the cell suspension was slowly injected. After cells were injected, the needle was left in the burrhole for 1–2 minutes to allow for complete delivery of the cells. The skull was cleaned and the skin was closed with 2 to 3 sutures. Animals were observed for recovery from surgery and anesthesia. Throughout the experiment, animals were observed at least twice each day for development of symptoms associated with progression of intracerebral tumor. Animals displaying advanced symptoms (leaning, loss of balance, dehydration, loss of appetite, loss of coordination, cessation of grooming activities, and/or significant weight loss) were humanely sacrificed and the organs and tissues of interest were resected.

Intraperitoneal Model.

Cell lines were grown in the appropriate media. Cells were harvested and washed in sterile PBS or medium without FBS, resuspended to a suitable concentration, and injected into the IP cavity of mice of the appropriate strain. Mice were observed daily for the occurrence of ascites formation. Individual animals were sacrificed when they presented with a weight gain of 40%, or when the IP tumor burden began to cause undue stress and pain to the animal.

Immunohistochemistry.

Acetone-fixed, 5 um frozen tissue sections untreated xenograft tumors derived from human, rat, or murine tumor cells were analyzed by immunohistochemistry using highly specific receptor antibodies. Briefly, non-specific binding sites were blocked with 10% normal goat serum prior to the application of the primarily antibody. Appropriate antibody concentrations were used to achieve the desired sensitivity and specificity (rabbit anti-human PDGF-B receptor 1:400, and affinity purified rabbit anti-mouse FLK-1 5.5 ug/ml). Tissue sections known to contain the protein of interest served as positive controls. Appropriate negative controls of normal rabbit IgG and mouse anti-chicken IgG of the same protein concentration and isotype as the primary antibodies were used. The detection method was a three-step indirect procedure and consisted of the primary antibody bound to a biotin labeled secondary antibody (goat anti-rabbit IgG 1:500) followed by streptavidin conjugated horseradish peroxidase. Diaminobenzidine/0.03% hydrogen peroxide (1:200) (0.05%) was used as the chromogen/substrate. Tissue sections were counterstained with hematoxylin, dehydrated through ascending grades of ethanol, cleared in Xylene Substitute, and coverslipped with Permount for microscopic evaluation. A "+" to "+++" grading system was used to identify the overall intensity of the expression. One plus ("+") reflects low intensity. Two pluses ("++") relates to medium intensity and three pluses ("+++") relates to high intensity. "T" is used in Table 4, below, to designate a tumor cell-specific staining reaction. "V" is used in the Table 4, below, to indicate a vascular endothelial cell-specific staining reaction. "*" is used above to indicate that the analysis was carried out using cytospins from the indicated cell lines. "NS" refers to "not significant" and "NT" refers to "not tested."

7.2. Experimental Results

Acetone-fixed frozen sections from xenograft tumors derived from human or murine tumor cell lines were analyzed by immunohistochemistry (IHC), as discussed above, using highly specific receptor antibodies to determine which tumor cell lines expressed the FLK-1 receptor. Specifically, the antibodies were obtained according to the procedure set forth at U.S. application Ser. No. 08/193,829. The results of the IHC analysis is set forth at Table 4:

TABLE 4

IHC Analysis of Tumors

| Tumor | FLK-1 | % Inhibition |
|---|---|---|
| C6 | ++ (V) | >95% |
| SKOV3T | NT | >95% |
| D1B | NT | 95% |
| SF763T | NT | 85% |
| U87MG | NT | 75% |
| L1210 | NT | 75% |
| PC-3 | +/++ (V) | 71% |
| SF767T | NT | 70% |
| U118T | NT | 57% |
| Calu-6 | ++/+++ (V) | 64% |
| U373MG | NT | 54% |
| PA-1 | ++ (V) | 53% |
| A375 | ++/+++ (V) | 53% |
| A431 | —* | NS |
| MCF7 | — | NS |
| A549 | NT | NS |

TABLE 4-continued

IHC Analysis of Tumors

| Tumor | FLK-1 | % Inhibition |
|---|---|---|
| MCF7/HER2 | — | NT |
| SKOV | NT | NT |

The in vivo experiments described above were then performed using the tumor cell lines which expressed FLK-1. The results were obtained in the above-described in vivo experiments are set forth at Table 4.

TABLE 5

Effect Of Compound 40 On Tumor Growth In Vivo

| Tumor Type | Cell Line | Strain | Dose mg/kg/day | % Inhibition (day) | P< |
|---|---|---|---|---|---|
| ovarian | PA-1 | nu/nu | 20 | 53 (36) | 0.04 |
| melanoma | A375 | nu/nu | 20 | 53 (31) | 0.03 |
| melanoma | A375 | SCID (day 9) | 15 | 53 (31) | 0.002 |
| prostate | PC-3 | nu/nu | 20 | 71 (45) | 0.01 |
| prostate | PC-3 | SCID (day 15) | 12 | 47 (36) | 0.001 |
| lung | Calu-6 | nu/nu | 20 | 64 (28) | 0.0001 |

These studies show a significant inhibition of tumor growth in immunocompetent animals treated with Compound 40. Specifically, as set forth above, Compound 40 effectively inhibited the growth of human ovarian (PA-1), human melanoma (A375), human prostate (PC-3), and human lung (Calu-6).

The studies were repeated to test additional compounds, including Compound 23. Compound 23 exhibited 41% inhibition at 20 mg/kg/day. More specifically, the results observed are set forth at Table 5.

TABLE 6

Effect Of Compounds In Vivo

| Compound | CALU-6 mg/kg/day |
|---|---|
| 4 | no significant inhibition @ 20 |
| 23 | 41% inhibition @ 20 |
| 12 | no detectable inhibition @ 20 |
| 2 | no detectable inhibition at 20 or 40 |
| 40 | 63.9% inhibition @ 20 |

The apparent lack of inhibition for some of the tested compounds does not necessarily indicate lack of activity (inhibition of angiogenesis and/or vasculogenesis) and may be explained by, for example, the half-life of the compound tested in vivo or the dose administered in the experiments.

8. EXAMPLES: In Vivo VEGF Pellet Model

In this model, VEGF is packaged into a time-release pellet and implanted subcutaneously on the abdomen of nude mice to induce a 'reddening' response and subsequent swelling around the pellet. Potential FLK-1 inhibitors may then be implanted in methylcellulose near the VEGF pellet ito determine whether such inhibitor may be used to inhibit the "reddening" response and subsequent swelling.

8.1. Materials And Methods

Materials.

The following materials were used:

1) VEGF- human recombinant lyophilized product is commercially may be obtained from Peprotech, Inc., Princeton Business Park, G2; P.O. box 275, Rocky Hill, N.J. 08553.

2) VEGF packaged into 21 day release pellets were obtained from Innovative Research of America, using patented matrix driven delivery system. Pellets were packaged at 0.20, 0.21, or 2.1 μg VEGF/pellet.

These doses approximate 10 and 100 ng/day release of VEGF. (Innovative Research of America, 3361 Executive Parkway, P.O. box 2746, Toledo, Ohio 43606)

3) Methylcellulose

4) Water (sterile)

5) Methanol

6) Appropriate drugs/inhibitors 7) 10 cm culture plates 8) parafilm

Protocol.

The following protocol was then followed to conduct the VEGF pellet model:

1) VEGF, purchased from Peprotech, was sent to Innovative Research for Custom Pellet preparation;

2) Methylcellulose prepared at 1.5% (w/v) in sterile water;

3) Drugs solublized in methanol (usual concentration range=10 to 20 mg/ml);

4) Place sterile parafilm in sterile 10 cm plates;

5) 150 μl of drug in methanol added to 1.35 ml of 1.5% methylcellulose and mixed/vortexed thoroughly;

6) 25 μl aliquots of homogenate placed on parafilm and dried into discs;

7) Mice (6–10 wk. Balb/C athymic nu/nu, female) were anesthetized via isoflurane inhalation;

8) VEGF pellets and methylcellulose discs were implanted subcutaneously on the abdomen; and 9) Mice were scored at 24 hours and 48 hours for reddening and swelling response.

The specific experimental design used in this example was:

N=4 animals/group

Controls:

VEGF pellet+drug placebo

VEGF placebo+drug pellet 8.2. Experimental Results

Compounds 5 and 15 were tested for activity according to the above-described protocol. Both compounds inhibited the "reddening" response and subsequent swelling indicating an inhibition of blood vessel formation and demonstrated activity against the FLK-1 receptor.

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

All references cited herein are hereby incorporated by reference in their entirety.

What is claimed:

1. A compound having the formula:

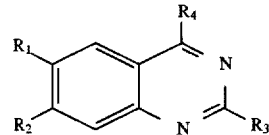

or a pharmaceutically acceptable salt thereof, wherein:

$R_1$ is $OCH_3$, $CH_3$ or H, $R_2$ is $OCH_3$ or H, $R_3$ is H or chloro, and $R_4$ is (4-methylphenyl)mercapto.

2. The compound of claim 1, wherein $R_1$ is $CH_3$ or H, and $R_2$ is H.

3. The compound of claim 2, wherein $R_3$ is chloro.

4. A compound having the formula:

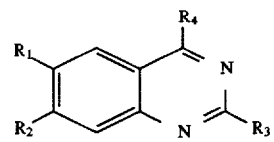

or a pharmaceutically acceptable salt thereof, wherein:

$R_1$ is $OCH_3$, $CH_3$ or H, $R_2$ is $OCH_3$ or H, $R_3$ is chloro, and $R_4$ is (4-methylphenyl)mercapto or (3-hydroxyphenyl)amino.

5. The compound of claim 4, wherein $R_1$ is $CH_3$ or H, and $R_2$ is H.

6. The compound of claim 5, wherein $R_4$ is (3-hydroxyphenyl)amino.

7. A pharmaceutical composition comprising a compound of claim 1, 2, 3, 4, 5, or 6 and a pharmaceutical carrier or excipient.

8. The pharmaceutical composition of claim 7, wherein said carrier is VPD:D5W.

9. A method for modulating vasculogenesis or angiogenesis which comprises administering to a human an effective amount of a compound of claim 1, 2, 3, 4, 5, or 6.

10. A method for modulating vasculogenesis or angiogenesis in a human having a non-cancer disorder, which comprises administering to said human an effective amount of a compound having the formula:

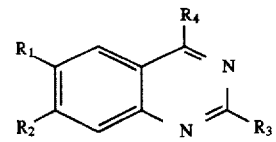

or a pharmaceutically acceptable salt thereof, wherein:

$R_1$ is $OCH_3$, $CH_3$ or H, $R_2$ is $OCH_3$ or H, $R_3$ is H or chloro, and $R_4$ is (3-chlorophenyl)amino, (4-methylphenyl)mercapto, (4-iodophenyl)amino or (3-hydroxyphenyl)amino.

11. The method of claim 10, wherein:

$R_1$ is $CH_3$ or H;

$R_2$ is $OCH_3$ or H; and $R_4$ is (4-methylphenyl)mercapto or (3-hydroxyphenyl)amino.

12. The method of claim 10, wherein said non-cancer disorder is selected from the group consisting of diabetes, diabetic retinopathy, rheumatoid arthritis and hemangioma.

* * * * *